(12) United States Patent
Suga et al.

(10) Patent No.: US 10,435,439 B2
(45) Date of Patent: Oct. 8, 2019

(54) PEPTIDE WITH SAFER SECONDARY STRUCTURE, PEPTIDE LIBRARY, AND PRODUCTION METHODS FOR SAME

(71) Applicant: The University of Tokyo, Tokyo (JP)

(72) Inventors: Hiroaki Suga, Tokyo (JP); Takashi Higuchi, Tokyo (JP)

(73) Assignee: The University of Tokyo, Tokyo (JP)

( * ) Notice: Subject to any disclaimer, the term of this patent is extended or adjusted under 35 U.S.C. 154(b) by 204 days.

(21) Appl. No.: 15/489,618

(22) Filed: Apr. 17, 2017

(65) Prior Publication Data

US 2017/0247416 A1    Aug. 31, 2017

Related U.S. Application Data

(62) Division of application No. 13/990,123, filed as application No. PCT/JP2011/078028 on Dec. 5, 2011, now Pat. No. 9,657,289.

(30) Foreign Application Priority Data

Dec. 3, 2010  (JP) ................. 2010-270958
May 20, 2011  (JP) ................. 2011-113527

(51) Int. Cl.
- *C40B 40/10* (2006.01)
- *C07K 14/00* (2006.01)
- (Continued)

(52) U.S. Cl.
CPC .......... *C07K 14/001* (2013.01); *C07C 229/08* (2013.01); *C07K 1/107* (2013.01);
(Continued)

(58) Field of Classification Search
None
See application file for complete search history.

(56) References Cited

U.S. PATENT DOCUMENTS

| 6,258,558 B1 | 7/2001 | Szostak et al. |
| 2003/0022230 A1 | 1/2003 | Yanagawa et al. |

(Continued)

FOREIGN PATENT DOCUMENTS

| JP | 3683282 B2 | 8/2005 |
| JP | 3683902 B2 | 8/2005 |
| JP | 3692542 B2 | 9/2005 |

OTHER PUBLICATIONS

Richard W. Roberts, et al., RNA-peptide fusions for the in vitro selection of peptides and proteins, The National Academy of Sciences, vol. 94, Nov. 1997, pp. 12297-12302.
(Continued)

*Primary Examiner* — Christian C Boesen
(74) *Attorney, Agent, or Firm* — Suzannah K. Sundby, Esq.; Canady + Lortz LLP

(57) ABSTRACT

An object of the invention is to provide a peptide having a stabilized secondary structure.
The present invention provides a peptide having a secondary structure stabilized by a crosslinked structure and containing at least one combination of a special amino acid of the formula (I):

[Chemical formula 1]

(Continued)

(wherein, (A) represents a single bond or a linking group having, in the main chain thereof, from 1 to 10 atoms;

(B) represents a group containing at least one π bond;

(C) represents a hydrogen atom or an alkyl group which may be substituted with a substituent; and X represents a group substitutable by a substitution reaction with a sulfanyl group) and an amino acid having, in the side chain thereof, a sulfanyl group; and having the crosslinked structure formed through a thioether bond between the side chain of the special amino acid residue and the sulfanyl group.

15 Claims, 6 Drawing Sheets

Specification includes a Sequence Listing.

(51) Int. Cl.

| | | |
|---|---|---|
| *C12P 11/00* | (2006.01) | |
| *C12P 21/02* | (2006.01) | |
| *C07K 1/107* | (2006.01) | |
| *C07K 2/00* | (2006.01) | |
| *C12N 15/10* | (2006.01) | |
| *C07C 229/08* | (2006.01) | |
| *G01N 33/68* | (2006.01) | |
| *A61K 38/00* | (2006.01) | |

(52) U.S. Cl.
CPC ............ *C07K 2/00* (2013.01); *C12N 15/1062* (2013.01); *C12P 11/00* (2013.01); *C12P 21/02* (2013.01); *G01N 33/6845* (2013.01); *A61K 38/00* (2013.01); *C40B 40/10* (2013.01)

(56) References Cited

U.S. PATENT DOCUMENTS

2008/0166766 A1 7/2008 Liu et al.
2010/0168380 A1 7/2010 Suga et al.

OTHER PUBLICATIONS

Naoto Nemoto, et al., In vitro virus: Bonding of mRNA bearing puromycin at the 3'-terminal end to the C-terminal end of its encoded protein on the ribosome in vitro, Federation of European Biochemical Societies, 1997, pp. 405-408.

Clay Bracken, et al., Synthesis and Nuclear Magnetic Resonance Structure Determination of an a-Helical, Bicylic, Lactam-Bridged Hexapeptide, Journal of American Chemical Society, 1994, pp. 6431-6432.

David Y. Jackson, et al., General Approach to the Synthesis of Short a-Helical Peptides, Journal of American Chemical Society, 1991, pp. 9391-9392.

J. Christopher Phelan, et al., A General Method for Constraining Short Peptides to an a-Helical Conformation, Journal of American Chemical Society, vol. 119; No. 3, Jan. 22, 1997, pp. 455-460.

Helen E. Blackwell, et al., Highly Efficient Synthesis of Covalently Cross-Linked Peptide Helices by Ring-Closing Metathesis, Angewandte Chemie International Edition, vol. 37; No. 23, 1998, pp. 3281-3284.

Loren D. Walensky, et al., Activation of Apoptosis in Vivo by Hydrocarbon-Stapled BH3 Helix, American Association for the Advancement of Science, vol. 305, 2004, pp. 1466-1470.

Hayashi, et al, "Ribosomal synthesis of nonstandard cyclic peptides and its application to drug discovery", 2010, pp. 505-514, vol. 82, No. 6, Publisher: The Jounal of Japanese Biochemical Society (English translation of excerpt).

Jansen, et al., "Studies on polypeptides. Part VII, : Synthesis of DL-, L- and D-2-amino-6-dimethylamino-4-hexynoic acid", 1969, pp. 819-827, vol. 88, No. 7, Publisher: RECUEIL.

Sako, et al., "Ribosomal Synthesis of Bicyclic Peptides via Two Orthogonal Inter-Side-Chain Reactions", 2008, pp. 7232-7234, vol. 130, No. 23, Publisher: J. Am. Chem. Soc.

International Search Report received in PCT/JP2011/078028 dated Mar. 6, 2012.

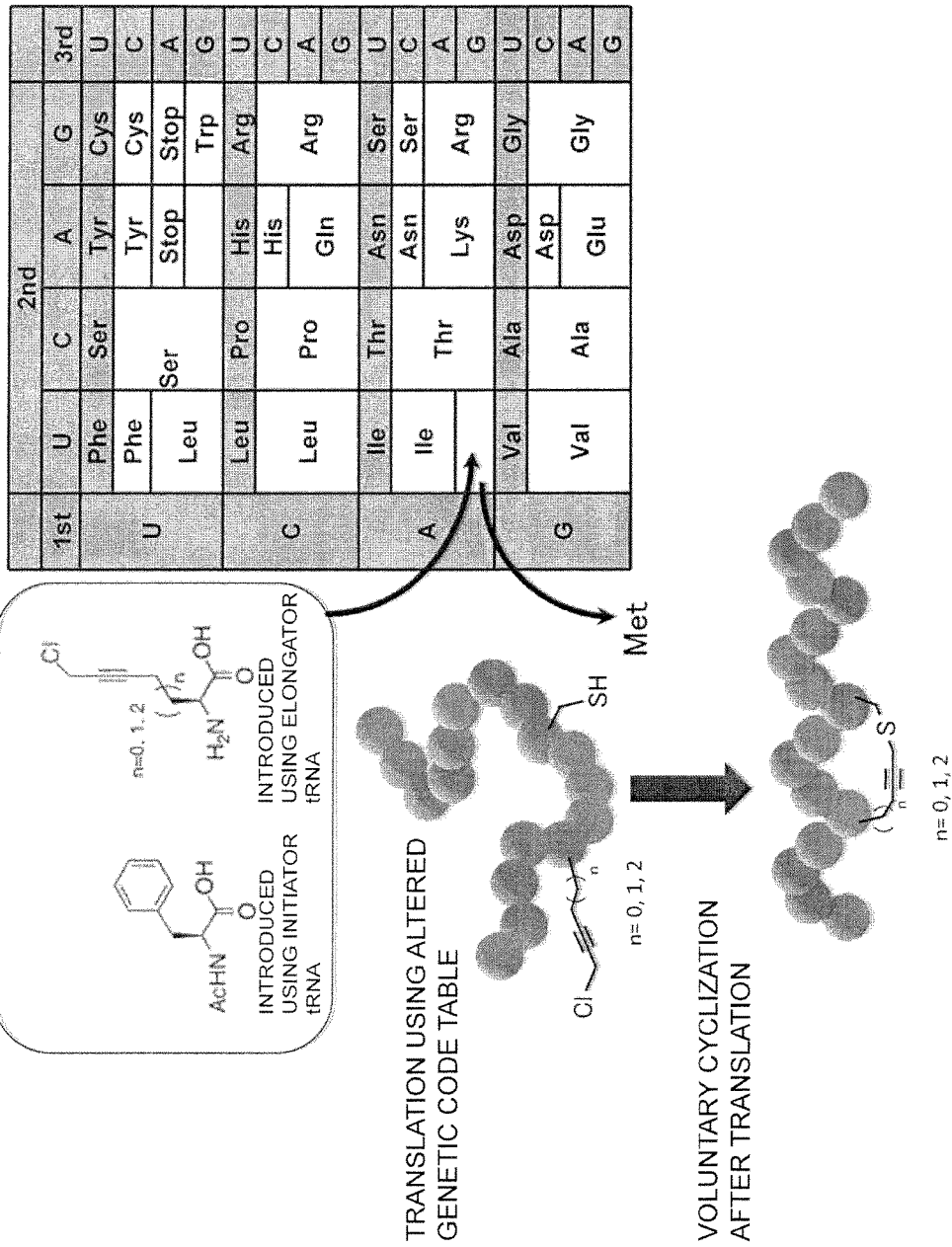

PEPTIDE WITH SAFER SECONDARY STRUCTURE, PEPTIDE LIBRARY, AND PRODUCTION METHODS FOR SAME

REFERENCE TO A SEQUENCE LISTING SUBMITTED VIA EFS-WEB

The content of the ASCII text file of the sequence listing named "20170417_034574_001DIV1_seq_ST25" which is 42.8 kb in size was created on Feb. 23, 2016, and electronically submitted via EFS-Web on Apr. 17, 2017, is incorporated herein by reference in its entirety.

TECHNICAL FIELD

The present invention relates to a peptide molecule having a fixed secondary structure induced by introducing a special amino acid(s), synthesis of the peptide molecule, a method of constructing a library composed of groups of such peptide molecules, a library thus constructed, and a method of screening an active peptide from the library.

BACKGROUND ART

As inhibitory molecular species against interaction between biological molecules, a peptide having an α helix secondary structure has attracted attentions mainly from the following three points. First one is that many interactions are mediated by an α helix so that development of an inhibitor making use of this structure as a starting point can be expected; second one is that since the peptide having a helix structure therein has cell membrane permeability with high possibility, a peptide drug targeting an intracellular protein can be created; and third one is that since in spite that it is a peptide, it has acquired stability against protease, it is expected to have a longer half-life in blood than general peptides. In most cases, however, preparation of a peptide simply based on the information of the amino acid sequence constituting the α helix does not lead to acquisition of such advantages. In the case of short-chain peptides, different from proteins having a three-dimensional structure, the circumstance surrounding the helix is exposed to a solvent and therefore the peptides are significantly affected by it so that they cannot keep their structure. With a view to overcoming this problem, there have been many attempts to crosslink amino acid side chains at appropriate positions to each other through a covalent bond in order to support a specific hydrogen bond that constitutes this helix structure, and thereby maintain or fix the helix structure even in an aqueous solution. Many of such approaches however depend all the processes, including peptide synthesis, on chemical synthesis because a chemical catalyst is used to form a covalent bond of an artificial amino acid incorporated in a peptide chain. When special peptides having a fixed α helix secondary structure are required to have physiological activity, peptide drug candidates have so far been found by designing or constructing a low diversity focused library based on the sequence of the α helix site of existing proteins and evaluating the activity of each peptide.

For acquiring a peptidic molecule that binds to a specific target, on the other hand, a method of screening from a random peptide library has been used widely. The most common method is a peptide display method using a phage, but recently, a peptide display method without using biological species such as Escherichia coli has been employed. Described specifically, various in vitro display methods such as ribosome display method and mRNA display method making use of translation are excellent because a high diversity library can be constructed and screened in a tube in a short period of time. The term "in vitro display method" means a system facilitating concentration and amplification (selection) of active species by linking a phenotype and a genotype encoding the sequence thereof through a non-covalent bond or a covalent bond to display the phenotype on the genotype and using a replication system reconstructed in a test tube. The greatest characteristic of this system is that it is conducted without using a prokaryote or eukaryote as a medium so that a high-activity physiological substance can be isolated from a library having great diversity. As a typical comparison example, phage display using Escherichia coli as a replication medium enables selection from a library having diversity as high as $10^7$, while in vitro display enables selection from a library having diversity as high as $10^{12}$. Examples of the in vitro display include ribosome display, mRNA display, and RaPID display (unpublished international application PCT/JP2010/68549). As one example, mRNA display will next be described below.

The mRNA display method is a technology of binding a polypeptide to an mRNA which is a template thereof to match the amino acid sequence of the polypeptide to the nucleic acid sequence. By binding puromycin, which is an analogue of the end of acylated tRNA, to the 3' end of the mRNA via an appropriate linker and adding it to a translation reaction, puromycin penetrates in the A site of ribosome, forms a covalent bond with a peptide during elongation, and as a result, a peptide molecule which is a translation product links to the mRNA via puromycin (Patent Documents 1 to 3, Non-patent Documents 1 and 2).

Thus, the in vitro display enables screening of a peptide library having diversity as high as $10^{12}$, but only a peptide library composed only of proteinogenic amino acids has conventionally been constructed because the peptide library is constructed by making use of functions of living body. It is expected that if the diversity of the library is improved by incorporating a novel and non-native function in the structure of amino acids, a peptide library having a novel skeleton capable of stabilizing an α helix secondary structure, which is usually unstable, can be constructed and screened, and that it becomes possible to obtain peptides exhibiting high inhibitory ability, selectivity, stability, and the like which naturally-occurring simple peptide chains cannot achieve.

With recent development in technology called "genetic code expansion" or "reprogramming of genetic code", it has actually become possible to produce and screen a peptide library having special amino acids by using various display methods such as phage display.

In genetic code expansion, it becomes possible to synthesize proteins or peptides containing a special amino acid by making use of stop codons or artificial four-base codons which are not used for assignment of an amino acid in a natural translation system and allocating these codons to the special amino acid. The number of usable special amino acids is however limited because the number of stop codons or usable four-base codons is limited (substantially, three or less special amino acids).

Studies on peptides having a crosslinked structure introduced therein have been made extensively in order to stabilize the α helix. There is a report on the method making use of an amide bond, a disulfide bond, and alkene formation through a ring-closing metathesis reaction (Non-patent Document 3). Introduction of these covalent bonds induces a helix structure, but this method has generally a problem in in vivo stability. Described specifically, the amide structure or disulfide structure is easily cleaved by protease or under the reduction conditions so that using such a peptide as an inhibitor is disadvantageous. In order to overcome this disadvantage, a method using alkene formation is developed. The peptide having a crosslinked structure formed by this method is found to have activity in vivo (Non-patent Document 4). A physiologically active peptide having a crosslinked structure by using alkene formation is under development.

The development however needs tremendous labor because after construction of a focused library from known amino acid sequences by chemical synthesis, the position of the crosslinked structure not depriving physiological activity must be examined precisely. In addition, the peptide sequence obtained from the thus-designed focused library as described above cannot always be the best sequence. Unfortunately, it is difficult to apply the crosslinked reaction making use of alkene formation to the in vitro display method because it uses a chemical catalyst. Described specifically, the alkene formation should be conducted in the presence of factors such as ribosome, protein, and ATP necessary for the translation reaction. They may presumably deteriorate the translation reaction efficiency, making it difficult to construct a high-quality library. In order to discover a physiologically active special peptide having a fixed α helix structure and useful for wider-range of targets, development of a crosslinking method that can be applied to the in vitro display method is indispensable. What is necessary for the crosslinking method is that the crosslinking reaction occurs rapidly and at high selectivity under the conditions in a translation system and the crosslinked structure thus formed is not easily degraded in vivo.

PRIOR ART DOCUMENTS

Patent Documents

Patent Document 1: Japanese Patent No. 3683282 (International Publication WO98/16636)
Patent Document 2: Japanese Patent No. 3683902 (International Publication WO98/31700)
Patent Document 3: Japanese Patent No. 3692542

Non-patent Documents

Non-patent Document 1: Roberts et al., Proc. Natl. Acd. Sci. USA, 1997, 94, 12297-12302,
Non-patent Document 2: Nemoto et al., FEES Lett., 1997, 414, 405-408,
Non-patent Document 3: Taylor, W., J., Baum, J. et al., J. Am. Chem. Soc., Vol. 116, p. 6431-6432 (1994), Schultz, P. G. et al., J. Am. Chem. Soc., Vol. 113, p. 9391-9392 (1991), Phelan, J. C. et al., J. Am. Chem. Soc., Vol. 119, p. 455-460 (1197), Grubbs, R. H., Blackwell, H. E., Angew. Chem. Int. Ed. Vol. 37, p. 3281-3284 (1998)
Non-patent Document 4: Verdine, G. L., Korsmeyer, S. J. et al., Science, Vol 305, p.1466-1470 (2004)

SUMMARY OF THE INVENTION

Problem to be Solved by the Invention

An object of the present invention is to provide a peptide having a stabilized secondary structure which is obtained by translational introduction, into a peptide chain, of a special amino acid designed to spontaneously cause formation of a crosslinked structure under translational synthesis conditions.

Means for Solving the Problem

By making use of a special peptide synthesizing technology through genetic code reprogramming recently developed by the present inventors, a target special peptide having a fixed secondary structure is produced by translational synthesis by synthesizing a special peptide having a side chain reactive with cysteine having, in the side chain thereof, a sulfanyl group (—SH group) or an analogue of the cysteine (FIG. 1).

Prior to detailed description on the present invention, "genetic code reprogramming", the background art of the present invention, will next be outlined.

In biological translation, three base sequences (triplet) of mRNA code for one amino acid as a codon and a peptide corresponding to the sequence is synthesized. The assignment of the codon to the amino acid is conducted in the following two stages. (i) To the end of tRNA is linked an amino acid corresponding thereto via aminoacyl tRNA synthetase (ARS). (ii) The tRNA anticodon matches with the mRNA codon corresponding thereto and the amino acid on the tRNA is polymerized along the information of the mRNA to synthesize a peptide.

Such a correspondent relationship between the codon and anticodon has been almost universally determined and any one of 20 amino acids is allocated for individual 64 codons. The following is a universal genetic code table.

TABLE 1

| | | \multicolumn{8}{c}{Base of the second character} | |
| | | U | | C | | A | | G | |
| | | Codon | Amino acid | Codon | Amino acid | Codon | Amino acid | Codon | Amino acid | |
| U | | UUU | Phenylalanine | UCU | Serine | UAU | Tyrosine | UGU | Cysteine | U |
| | | UUC | Phenylalanine | UCC | Serine | UAC | Tyrosine | UGC | Cysteine | C |
| | | UUA | Leucine | UCA | Serine | UAA | Stop | UGA | Stop | A |
| | | UUG | Leucine | UCG | Serine | UAG | Stop | UGG | Tryptophan | G |
| C | | CUU | Leucine | CCU | Proline | CAU | Histidine | CGU | Arginine | U |
| | | CUC | Leucine | CCC | Proline | CAC | Histidine | CGC | Arginine | C |
| | | CUA | Leucine | CCA | Proline | CAA | Glutamine | CGA | Arginine | A |
| | | CUG | Leucine | CCG | Proline | CAG | Glutamine | CGG | Arginine | G |
| A | | AUU | Isoleucine | ACU | Threonine | AAU | Asparagine | AGU | Serine | U |
| | | AUC | Isoleucine | ACC | Threonine | AAC | Asparagine | AGC | Serine | C |
| | | AUA | Isoleucine | ACA | Threonine | AAA | Lysine | AGA | Arginine | A |
| | | AUG | Methionine | ACG | Threonine | AAG | Lysine | AGG | Arginine | G |

TABLE 1-continued

| | | | | | Base of the second character | | | | |
|---|---|---|---|---|---|---|---|---|---|
| | | U | | C | | A | | G | |
| | Codon | Amino acid | Codon | Amino acid | Codon | Amino acid | Codon | Amino acid | |
| G | GUU | Valine | GCU | Alanine | GAU | Aspartic acid | GGU | Glycine | U |
| | GUC | Valine | GCC | Alanine | GAC | Aspartic acid | GGC | Glycine | C |
| | GUA | Valine | GCA | Alanine | GAA | Glutamic acid | GGA | Glycine | A |
| | GUG | Valine | GCG | Alanine | GAG | Glutamic acid | GGG | Glycine | G |
| Base of the first character | | | | | | | | | Base of the third character |

The above genetic codes can be reprogrammed by using a reconstituted translation system and flexizyme, that is, an artificial aminoacylating RNA catalyst.

A reconstituted translation system is obtained by isolating and purifying factors relating to translational synthesis of a protein or peptide, such as ribosome, translation factors, tRNAs, amino acids, and energy sources such as ATP and GTP, respectively and then mixing them. For example, technologies described in the following documents as a system using a ribosome of *Escherichia coli* are known: H. F. Kung, B. Redfield, B. V. Treadwell, B. Eskin, C. Spears and H. Weissbach (1977) "DNA-directed in vitro synthesis of beta-galactosidase. Studies with purified factors" The Journal of Biological Chemistry Vol. 252, No. 19, 6889-6894; M. C. Gonza, C. Cunningham and R. M. Green (1985) "Isolation and point of action of a factor from *Escherichia coli* required to reconstruct translation" Proceeding of National Academy of Sciences of the United States of America Vol. 82, 1648-1652; M. Y. Pavlov and M. Ehrenberg (1996) "Rate of translation of natural mRNAs in an optimized in vitro system" Archives of Biochemistry and Biophysics Vol. 328, No. 1, 9-16; Y. Shimizu, A. Inoue, Y. Tomari, T. Suzuki, T. Yokogawa, K. Nishikawa and T. Ueda (2001) "Cell-free translation reconstituted with purified components" Nature Biotechnology Vol. 19, No. 8, 751-755;H. Ohashi, Y. Shimizu, B. W. Ying, and T. Ueda (2007) "Efficient protein selection based on ribosome display system with purified components" Biochemical and Biophysical Research Communications Vol. 352, No. 1, 270-276.

On the other hand, flexizyme is an artificial RNA catalyst (RNA catalyst having acyl tRNA synthetase-like activity) capable of linking (acylating) any amino acid or hydroxy acid to any tRNA. For example, those described in the following documents are known: H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature Methods 3, 357-359 "The flexizyme system: a highly flexible tRNA aminoacylation tool for the synthesis of nonnatural peptides"; N. Niwa, Y. Yamagishi, H. Murakami, H. Suga (2009) Bioorganic & Medicinal Chemistry Letters 19, 3892-3894 "A flexizyme that selectively charges amino acids activated by a water-friendly leaving group"; and WO2007/066627, "Multi-purpose acylation catalyst and use thereof". Flexizyme includes an original type flexizyme (Fx) and an altered type which is known as the name of dinitrobenzyl flexizyme (dFx), enhanced flexizyme (eFx) or amino flexizyme (aFx).

As a modified method capable of linking any amino acid to any tRNA, chemical aminoacylation or the like method can also be used.

For genetic code reprogramming, a translation system made by arbitrarily removing component factors from the translation system, depending on the purpose, and then reconstituting the necessary components is used. For example, when a translation system from which a specific amino acid(s) has (have) been removed is reconstituted, the codon(s) corresponding to the amino acid(s) becomes (become) an vacant codon(s). Next, by using flexizyme (or chemical aminoacylation or aminoacylation with a mutant protein enzyme), a special amino acid(s) is (are) linked to tRNA(s) having an anticodon(s) complementary to the vacant codon(s), followed by translation. As a result, the codon(s) codes (code) for the special amino acid(s) and a peptide in which the special amino acid(s) has (have) been introduced instead of the removed amino acid(s) is (are) obtained by translation.

As one mode of the present invention, which is not intended to limit the invention, for example, a special peptide having, in the side chain thereof, a propargyl chloride structure is synthesized by using genetic code reprogramming technology. If a cysteine residue is placed in the peptide while sandwiching an appropriate number of residues between the cysteine residue and the residue having the above-mentioned side-chain structure, a spontaneous substitution reaction proceeds on the propargyl position by the sulfanyl group after translation and a crosslinked structure through a thioether bond is formed between peptide side chains. This means that by incorporating, into an amino acid, a bond formable pair of a propargyl chloride structure as an electrophilic agent and a sulfanyl group as a nucleophilic agent, a bond is formed therebetween and a crosslinked structure can be constructed. This crosslinked structure helps a position-specific hydrogen bond which will be a key of helix formation to induce the helix structure and the resulting peptide has a desired secondary structure. Such a bond formable pair of molecular structures is not limited to the propargyl chloride structure and cysteine. Details will be described later.

Moreover, the present invention provides a technology of constructing a special peptide library by making use of the above-mentioned technology and obtaining an inhibitor of biological intermolecular interaction.

The following are the summary of the present invention.

[1] A peptide having a secondary structure stabilized by a crosslinked structure; having at least one combination of a special amino acid represented by the following formula (I):

[Chemical formula 1]

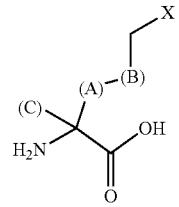

(I)

(in the formula, (A) represents a single bond or a linking group having, in the main chain thereof, from 1 to 10 atoms, (B) represents a group containing at least one π bond, (C) represents a hydrogen atom or an alkyl group which may be substituted with a substituent, and X represents a group substitutable by a substitution reaction with a sulfanyl group) and an amino acid having in the side chain thereof a sulfanyl group; and having the crosslinked structure formed through a thioether bond between the side chain of the special amino acid residue and the sulfanyl group.

[2] The peptide as described above in [1], wherein in the formula (I), (A) is selected from the class consisting of a single bond, alkylene groups having from 1 to 10 carbon atoms, alkenylene groups having from 2 to 10 carbon atoms, and alkynylene groups having from 2 to 10 carbon atoms, which may be substituted with a substituent; and alkylene groups, alkenylene groups, and alkynylene groups having, in the main chain thereof, 10 or less atoms, in which one or two carbon atoms in the main chain have been substituted with an oxygen atom, a nitrogen atom, or a sulfur atom and which may be substituted with a substituent, (B) is selected from the class consisting of —C≡C—, —C=C—, —Ar—, —Ar—Ar—, —Ar—C≡C—, —Ar—C=C—, —NHC(O)—, —C(O)—, —Ar—NHC(O)—, and —Ar—C(O)—, (C) is selected from the class consisting of hydrogen, a methyl group, an ethyl group, a propyl group, a butyl group, and a pentyl group, and X is selected from the class consisting of Cl, Br, I, —OSO$_2$Me, a tosyl group, a nosyl group, and —OSO$_2$—Ar—R (wherein, R represents a group selected from the class consisting of CH$_3$, NO$_2$, CF$_3$, and H).

[3] The peptide as described above in [1] or [2], wherein the special amino acid in the above formula (I) is represented by any one of the following formulas (II) to (IV):

[Chemical formula 2]

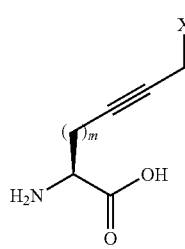

(II)

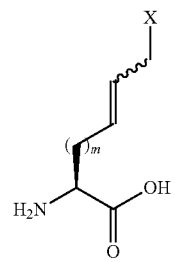

(III)

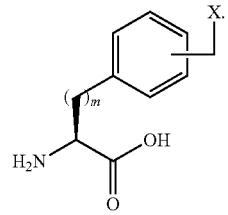

(IV)

[in the formula, m represents an integer selected from 1 to 10 and X is selected from the group consisting of Cl, Br, I, —OSO$_2$Me, a tosyl group, a nosyl group, and —OSO$_2$—Ar—R (wherein, R represents a group selected from the class consisting of CH$_3$, NO$_2$, CF$_3$ and H)].

[4] The peptide as described above in any one of [1] to [3], wherein the amino acid having a sulfanyl group is selected from the group consisting of cysteine and cysteine analogues represented by the following formulas (V) and (VI):

[Chemical formula 3]

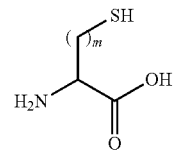

(V)

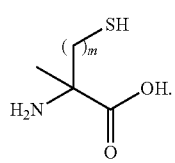

(VI)

[5] The peptide as described above in any of [1] to [4], wherein the special amino acid residue and the amino acid residue having, in the side chain thereof, a sulfanyl group are, in each combination, placed with 2, 3, 6, or 10 amino acid residues therebetween.

[6] A process of preparing a peptide having a secondary structure stabilized with a crosslinked structure, including:

(i) a step of translationally synthesizing a special peptide having, in the molecule thereof, at least one combination of an amino acid having, in the side chain thereof, a sulfanyl group and a special amino acid represented by the following formula (I):

[Chemical formula 4]

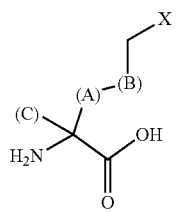
(I)

[in the formula, (A) represents a single bond or a linking group having, in the main chain thereof, from 1 to 10 atoms; (B) represents a group containing at least one π bond; (C) represents a hydrogen atom or an alkyl group which may be substituted with a substituent; and X represents a group substitutable by a substitution reaction with a sulfanyl group); and (ii) a step of forming a thioether bond between the sulfanyl group and the side chain of the special amino acid of the formula (I) in each combination to form a crosslinked structure.

[7] The process as described above in [6], wherein the amino acid having, in the side chain thereof, a sulfanyl group and the special amino acid of the formula (I) are, in each combination, placed with 2, 3, 6, or 10 amino acid residues therebetween.

[8] The process as described above in [6] or [7], wherein the translational synthesis step (i) includes making use of aminoacyl-tRNA available by linking the special amino acid of the formula (I) to tRNA and thereby translating a template mRNA having an altered codon encoding the special amino acid.

[9] The process as described above in [8], wherein the amino acid having, in the side chain thereof, a sulfanyl group is a special amino acid encoded by an altered codon and the translational synthesis step (i) includes making use of aminoacyl tRNA available by linking the special amino acid of the formula (I) and the special amino acid having, in the side chain thereof, a sulfanyl group to tRNA, respectively, and thereby translating a template mRNA having an altered codon encoding the respective special amino acids.

[10] The process as described above in [8] or [9], wherein the aminoacyl tRNA is obtained by linking the special amino acid to tRNA by using an RNA catalyst having an aminoacyl-tRNA synthetase-like activity.

[11] The process as described above in any of [6] to [10], wherein the special amino acid represented by the formula (I) is represented by any of the following formulas (II) to (IV);

[Chemical formula 5]

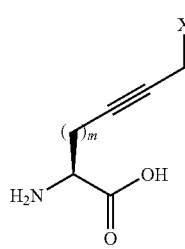
(II)

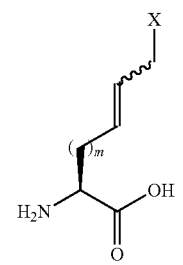
(III)

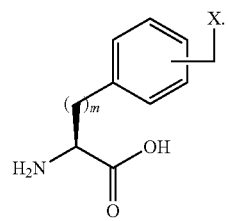
(IV)

[12] The process as described above in any of [6] to [11], wherein the amino acid having a sulfanyl group is selected from the group consisting of cysteine and cysteine analogues represented by the following formulas (V) and (VI);

[Chemical formula 6]

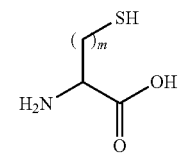
(V)

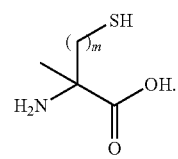
(VI)

[13] A peptide library including two or more kinds of the peptide as described above in any one of [1] to [5].

[14] The peptide library as described above in [13], wherein each of the peptides is linked to an mRNA encoding the peptide.

[15] A method of constructing the peptide library as described above in [13], including:

(i) a step of producing an mRNA library which contains at least one combination of a codon encoding an amino acid having, in the side chain thereof, a sulfanyl group and a codon encoding the special amino acid represented by the formula (I) as described above in [1] in an RNA encoding a random amino acid sequence; in each combination, the codon encoding an amino acid having, in the side chain thereof, a sulfanyl group and the codon encoding the special amino acid of the formula (I) being placed with 2, 3, 6, or 10 amino acid units therebetween; and (ii) a step of translating the mRNA by using a cell-free translation system containing a tRNA to which the special amino acid has been linked and thereby obtaining a group of peptides having the special amino acid placed in the random sequence; and (iii) a step of forming, in each of the peptides, a crosslinked structure by binding the sulfanyl group to the side chain of the special amino acid of the formula (I).

[16] A method of constructing the peptide library as described above in [14], including
a step of, in the step (i) as described above in [15], binding puromycin to the 3'-end of the mRNA to obtain a puromycin-bound mRNA library;
a step of, in the step (ii), causing the puromycin-bound mRNA library to express in a cell-free translation system to obtain a peptide-mRNA complex having the special amino acid placed in the random sequence; and
a step of conducting the step (iii).

[17] The method as described above in [15] or [16], wherein an altered codon encoding the special amino acid of the formula (I) is AUG codon and the mRNA random sequence is composed of repetition of a triplet of either one of an NNC or NNU sequence (N represents any one base of A, U, G, and C).

[18] A special amino acid represented by the following formula (I);

[Chemical formula 7]

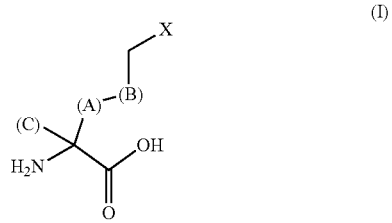

(I)

[in the formula, (A) represents a single bond or a linking group having from 1 to 10 atoms in the main chain; (B) represents a group containing at least one carbon-carbon double bond, a group containing at least one carbon-carbon triple bond, or a group containing at least an aromatic ring; (C) represents a hydrogen atom or an alkyl group having from 1 to 3 carbon atoms which may be substituted with a substituent; and X represents a group substitutable by a substitution reaction with a sulfanyl group].

[19] A method of selecting a peptide binding to a target protein from the peptide library as described above in [13] or [14], including:
(i) a step of bringing the peptide library into contact with the target protein, followed by incubation; and
(ii) selecting a peptide molecule that binds to the target protein.

[20] A method of selecting, from the peptide library as described above in [13] or [14], a peptide having inhibitory activity against the intermolecular interaction of a target protein, including:
(i) primary screening, including the steps (i) and (ii) as described above in [19], for selecting a peptide that binds to the target protein; and
(ii) secondary screening for evaluating inhibitory activity of the peptide, which has been selected in the primary screening (i), against intermolecular interaction of the target protein and thereby determining that the peptide has inhibitory activity against the intermolecular interaction of the target protein.

[21] A process of preparing a peptide that binds to a target protein:
(i) a step of bringing the peptide library as described above in [14] into contact with the target protein while incubating;
(ii) a step of selecting a peptide-mRNA complex that binds to the target protein;
(iii) a step of amplifying the mRNA of the selected peptide-mRNA complex to obtain a peptide-mRNA complex;
(iv) repeating the steps (i) to (iii) at least once to concentrate the peptide-mRNA complex having high-affinity; and
(v) causing the mRNA of the peptide-mRNA complex concentrated in the step (iv) to express the peptide.

[22] The method as described above in either one of [19] or [20], wherein the target protein is a molecule that suppresses apoptosis.

Effect of the Invention

The present invention makes it possible to provide a peptide having a stabilized secondary structure (for example, α helix structure) because a crosslinked structure has been introduced at a desired position. Such a peptide has a stabilized secondary structure so that it has functions that typical peptides cannot have, for example, high affinity with a target, high selectivity, excellent cell membrane permeability, and excellent stability.

In addition, the present invention makes it possible to obtain a peptide(s) having high affinity with a target protein or the like or a peptide(s) having physiological activity such as peptide(s) inhibiting the function of a target protein, by constructing a peptide library composed of such peptides having randomized amino acid sequences and screening with this library.

The present invention also makes it possible to facilitate concentration and amplification of a selected peptide by linking, in a peptide library, the peptide and a nucleic acid encoding it and applying an in vitro display method.

For the graphs on the left side, the y-axis labels are "Intens. [a.u.]" and (a) for the top and bottom graphs, the y-axis major tick values are 0, 500, 1000, 1500, 2000, and 2500, (b) for the middle two graphs, the y-axis major tick values are 0, 250, 500, 750, 1000, and 1250, and the x-axis tick values from left to right are 500, 1000, 1500, 1500, 2000, 2500, 3000, and 3500 m/z.

For the graphs on the right side, the y-axis labels are "Intens. [a.u.]" and (a) for the top two graphs the major tick values are 0, 200, 400, 600, and 800, (b) for the third graph from the top the major tick values are 0, 200, 400, 600, 800, 1000, and 1200, and (c) for the bottom graph the major tick values are 0, 500, 1000, 1500, 2000, and 2500, and the x-axis tick values from left to right are 1800, 1820, 1840, 1860, 1880, 1900, 1920, and 1940 m/z.

Figure 4:
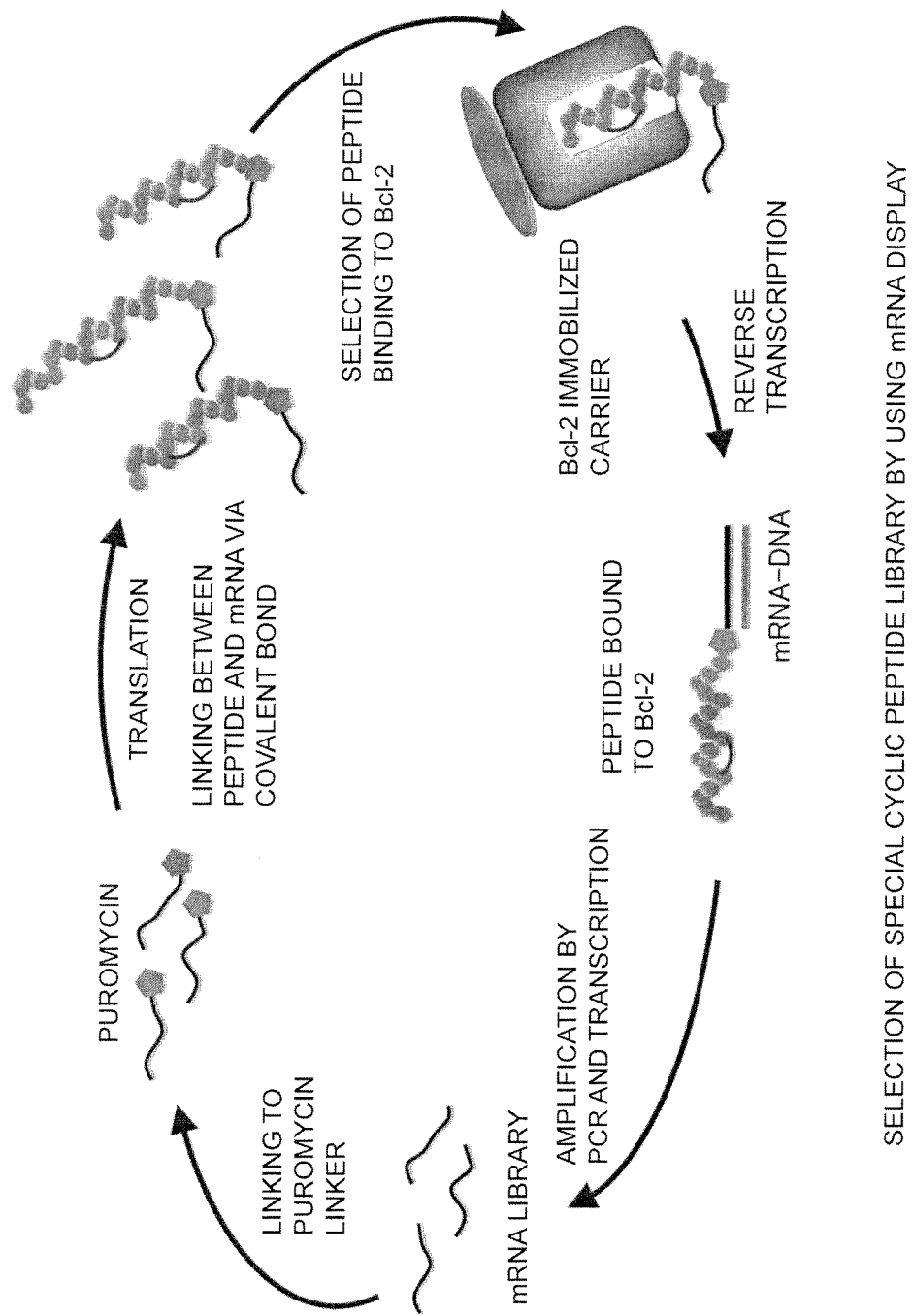

FIG. 4 shows the concept of screening using a crosslinked peptide library by using mRNA display.

Figure 5:
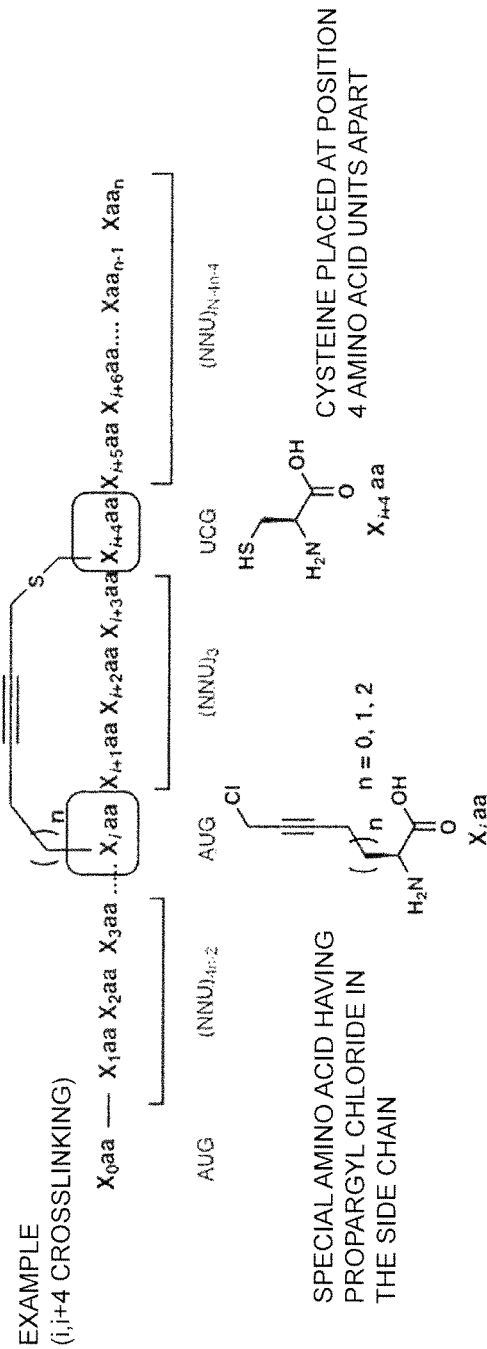

FIG. 5 shows a construction example of an mRNA library. mRNA sequences of Pools 16-1, 16-2, 20-1, 20-2, 20-3, 24-1, 24-2, 24-3, and 24-4 are set forth as SEQ ID NOs:31 to 39 in the Sequence Listing, respectively.

FIG. 6 shows the concept of translation under an altered genetic code table.

MODE FOR CARRYING OUT THE INVENTION

Peptide Having a Crosslinked Structure Introduced Therein

The present invention provides a novel peptide having a crosslinked structure and thereby having a more stabilized secondary structure. The term "secondary structure" as used herein is a special structure which is made of a hydrogen bond in the peptide main chain and can be observed in a relatively narrow region and it means a helix structure, β structure, or the like. The present invention is suited for stabilization of a helix structure such as α helix structure and $3_{10}$ helix structure, but can stabilize another secondary structure.

The term "stabilize the secondary structure" of a peptide as used herein means that the second structure is stabilized to the extent permitting binding of the peptide to a target molecule with certain reproducibility.

Stabilizing the second structure of a peptide by introducing therein a crosslinked structure is presumed to (i) improve protease resistance, (ii) improve membrane permeability, and (iii) improve affinity with a target protein. As described in the background art, there has been an attempt to stabilize the secondary structure of a peptide by crosslinking between amino acid side chains with an amide bond or disulfide bond. There is also a report on the crosslinking reaction through alkene formation in the presence of a chemical catalyst.

The crosslinked structure formed in the peptide of the present invention is, different from that formed in the conventional method, not easily degraded in vivo. More specifically, it is not enzymatically degraded like an amide bond or is not reduced like a disulfide bond.

The peptide of the present invention contains at least one combination of a special amino acid represented by the following formula (I) and an amino acid having, in the side chain thereof, a sulfanyl group and has a crosslinked structure through a thioether bond between the side chain of the special amino acid and the sulfanyl group.

[Chemical formula 8]

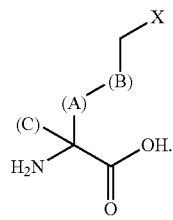

(I)

In the formula, (A) is a site functioning as a spacer. (A) is a single bond or a linking group having, in the main chain thereof, from 1 to 10 atoms. Although it is not limited insofar as a crosslinking reaction between (B) $CH_2$—X and a sulfanyl group, which will be described later, occurs smoothly, examples include, not limited thereto, a single bond, alkylene groups having from 1 to 10 carbon atoms, alkenylene groups having from 2 to 10 carbon atoms, and alkynylene groups having from 2 to 10 carbon atoms, which may be substituted with a substituent; and alkylene groups, alkenylene groups, and alkynylene groups having, in the main chain thereof, from not greater than 10 atoms, in which one or two carbon atoms in the main chain have been substituted with an oxygen atom, a nitrogen atom, or a sulfur atom and which may be substituted with a substituent.

It is to be noted that presence of (A) is advantageous because it is preferable for the progress of a translation reaction when the peptide of the present invention is synthesized by using translational synthesis.

Although (B) may represent any group insofar as it induces a substitution reaction of X with a sulfanyl group, examples include groups containing at least one π bond. Examples of the groups containing a π bond include alkylene groups, alkenylene groups, and alkynylene groups which may be substituted with a substituent; groups containing at least one aromatic ring, which may be substituted with a substituent; and groups containing at least one ketone or amide. The number of carbon atoms of (B) may be, when it is an alkylene group, an alkenylene group, or an alkynylene group, for example, from 1 to 10, from 2 to 8, or from 2 to 5. When it is a group containing at least one aromatic ring or a group containing at least one ketone or amide, the number of atoms in the main chain may be set at, for example, from 1 to 10, from 2 to 8, or from 2 to 5. Although the position of the π bond is not particularly limited insofar as the substitution reaction of X with a sulfanyl group proceeds smoothly, it is preferred that at least one atom constituting the π bond is bound to a carbon atom at which the substitution reaction with a sulfanyl group is made. It is most preferred that the π bond is located directly from a $CH_2$ group while sandwiching it with X.

Examples of (B) include, but not limited to, —C≡C—, —C═C—, —Ar—, —Ar—Ar—, —Ar—C≡C—, —Ar—C═C—, —NHC(O)—, —C(O)—, —Ar—NHC(O)—, and —Ar—C(O)—.

The following is an example of a crosslinked structure through a thioether bond between the sulfanyl group and the side chain of the special amino acid represented by the formula (I).

TABLE 2

| Reaction site (B) —$CH_2$X | Crosslinked structure |
| --- | --- |
| —C≡C—$CH_2$X | —C≡C—$CH_2$—S— |
| \C═C—$CH_2$ | \C═C═$CH_2$ |
|  | —S |
| \C═C\$CH_2$X | \C═C\$CH_2$—S— |
| \C—C\\\$CH_2$ |  |
| —S |  |
| \C═C/$CH_2$X | \C═C/$CH_2$—S— |
| \C—C\\\$CH_2$ |  |
| —S |  |
| —Ar—$CH_2$X | —Ar—$CH_2$—S— |

Although X is not particularly limited insofar as it is an atom or group eliminable by the substitution reaction with a sulfanyl group, it may be, for example, Cl, Br, I, —$OSO_2$Me, or —$OSO_2$—Ar—R (wherein, R represents a group selected from the class consisting of $CH_3$, $NO_2$, $CF_3$ and H).

(C) represents a hydrogen atom or an alkyl group which may be substituted with a substituent. Examples of it may include a methyl group, an ethyl group, a propyl group, a butyl group, and a pentyl group, which may be substituted with a substituent. It may be branched.

The term "alkenylene group" as used herein means an alkylene group having, in the main chain thereof, from 1 to 3 double bonds and the term "alkynylene group" means an alkylene group having, in the main chain thereof, from 1 to 3 triple bonds. The position of the double bond or triple bond is not particularly limited insofar as the peptide exhibits an intended effect.

Although the substituent herein is not particularly limited, examples include halogen atoms, alkyl groups with from 1 to 6 carbon atoms which may be substituted, alkoxy groups with from 1 to 6 carbon atoms which may be substituted, a cyano group, a nitro group, a hydroxy group, a carboxyl group, acyl groups, an amino group, aryl groups, heteroaryl groups, a phenoxy group, and non-aromatic heterocyclic groups.

Since in the peptide of the present invention, a crosslinked structure is formed through bond formation between the side chain portion of the special amino acid of the formula (I) and the sulfanyl group, it is necessary that the functional groups are present on different constituent units, where one amino acid residue, which is a constituent of the peptide, is considered as a unit, and are placed so as to stabilize the secondary structure when a crosslinked structure is formed. For the convenience of description, such a constituent unit is called "amino acid unit".

Figure 1:
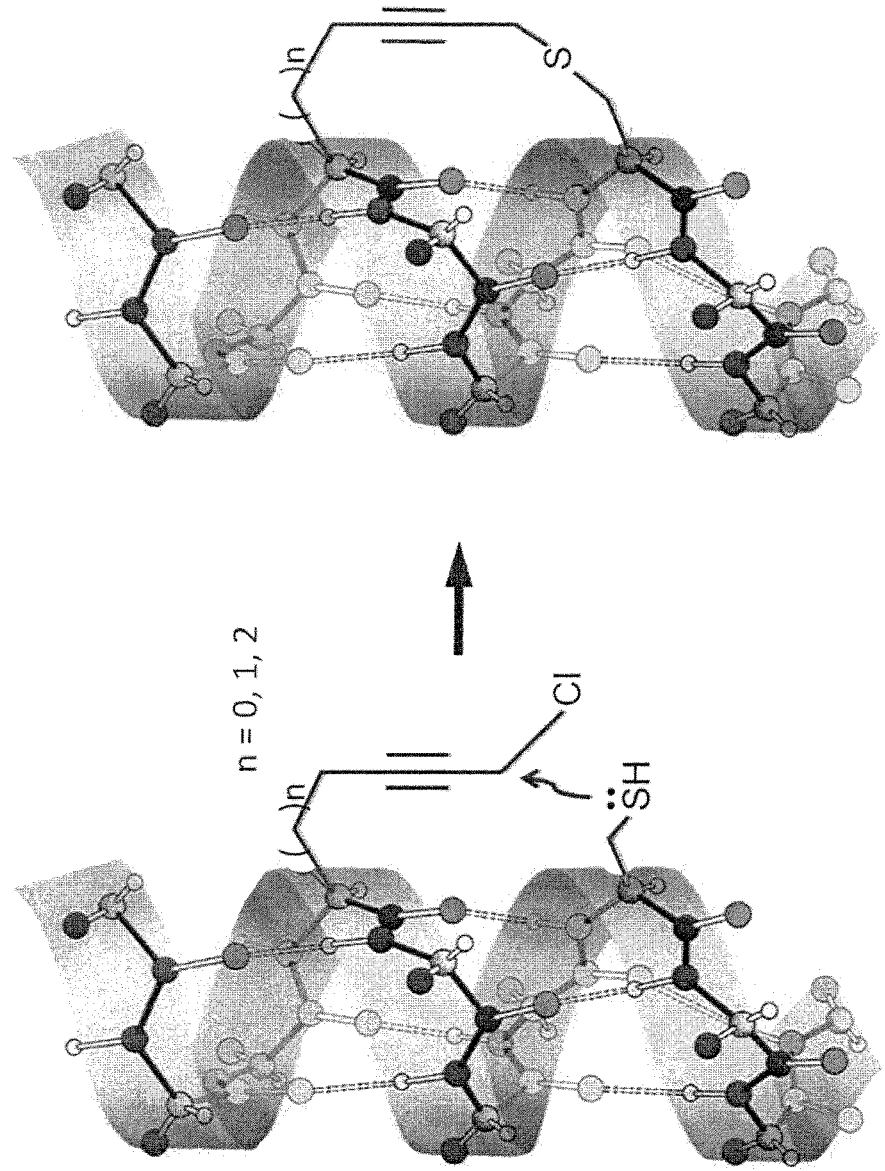
FIG. 1 shows one example of a special peptide having a fixed α helix secondary structure.
Figure 2:
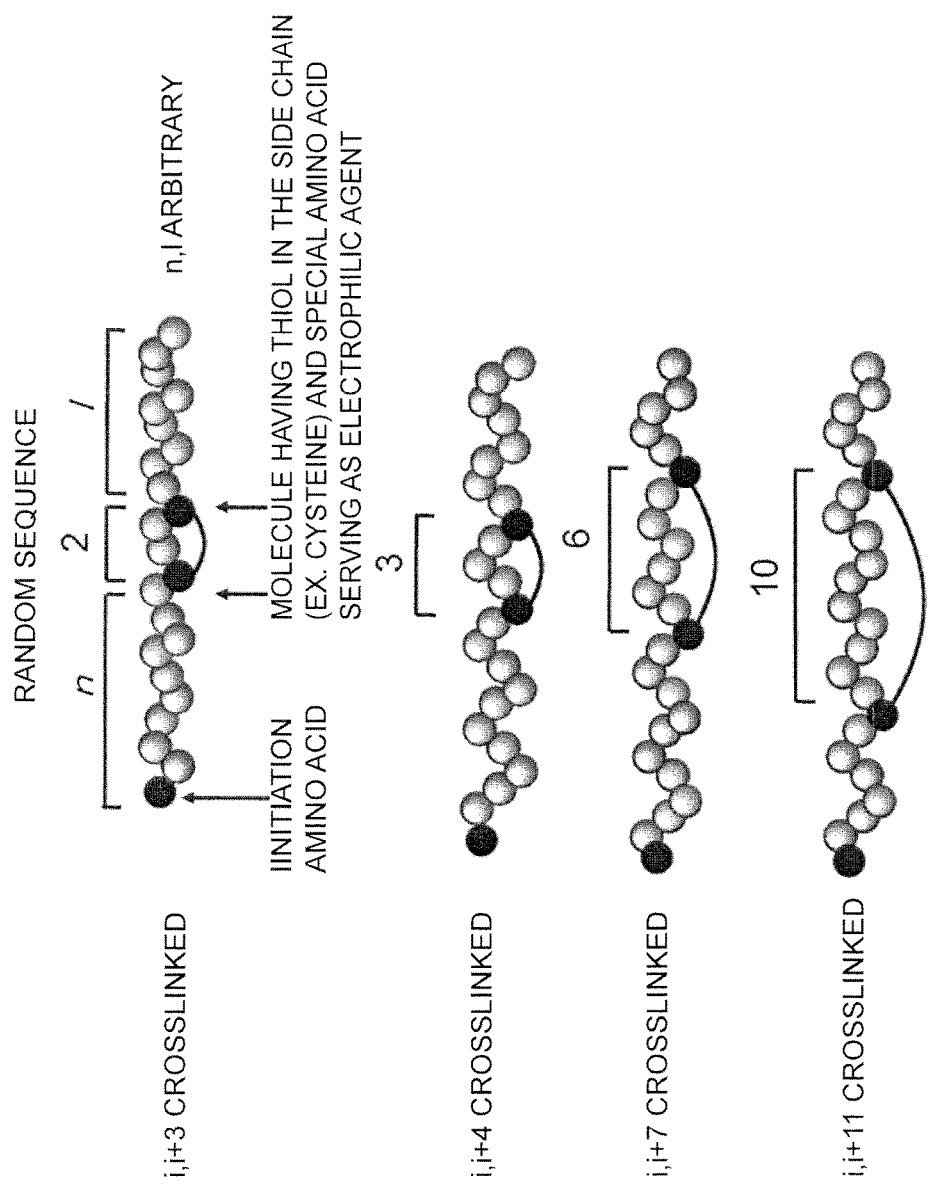
FIG. 2 shows an arrangement example in a crosslinked structure precursor.

An amino acid unit which will be an electrophilic agent (corresponding to a special amino acid) and an amino acid unit having a sulfanyl group are preferably placed at positions indicated by (i, i+3), (i, i+4), (i, i+7), or (i, i+11). Referring to FIG. 2, i represents any integer of 0 or greater and shows the position of an amino acid unit counted from the N-terminal residue of a peptide including a crosslinked structure precursor. For example, when i=3 and the amino acid unit which will be an electrophilic agent and the amino acid unit having a sulfanyl group are placed at the position of (i, i+4), they are placed at positions of three amino acid units and seven amino acid units from the N terminal (0 position), respectively to form a crosslinked structure.

When the crosslinked structure is formed at i+3 or i+4, one crosslink is formed at each turn in the case of α helix, while when the crosslinked structure is formed at i+7 or i+11, one crosslink is formed at every two turns or three turns. In other words, presence of 2, 3, 6, or 10 amino acid units between the amino acid units forming a crosslinked structure is preferred.

The amino acid unit located between, before, or after the amino acid units constituting a crosslinked structure is preferably any amino acid, except the initiation amino acid at the N terminal, which is a compound (aminocarboxylic acid) having in the molecule thereof, two functional groups, that is, an amino group (—NR$_2$) and a carboxyl group (—COOH). A typical one is α-aminocarboxylic acid, with a proteinogenic amino acid being more preferred. The positions of the amino acid unit which will be an electrophilic agent and the amino acid unit having a sulfanyl group are not determined and whichever can be placed on the N-terminal side.

The term "special amino acid" means any of amino acids different in structure from 20 proteinogenic amino acids to be used in a natural translation system and it may be either an artificially synthesized one or that occurring in nature. It embraces any of non-proteinogenic amino acids obtained by chemically altering or modifying a portion of the side chain structure of a proteinogenic amino acid, artificial amino acids, D-form amino acid, N-methylamino acid, N-acylamino acid, β-amino acid, and derivatives having a structure obtained by substituting an amino group or a carboxyl group on the amino acid skeleton. The term "special peptide" means a peptide in which two or more amino acids containing one or more special amino acids have been bound mainly via a peptide bond (it may sometimes contain a cyclic structure or an ester bond).

In the present invention, a typical example of the amino acid having a sulfanyl group is cysteine or an analogue thereof (cysteine analogue). A typical example of the amino acid reactive with it and serving as an electrophilic agent is the special amino acid of the formula (I). As described later, when the sulfanyl-containing amino acid is cysteine, a universal codon can be used, but when it is a non-proteinogenic amino acid, it is encoded with an altered codon. On the other hand, the special amino acid of the formula (I) is always encoded by an altered codon.

In the present invention, an initiation amino acid that will be a peptide-chain N-terminal is not limited to methionine and any proteinogenic amino acid other than methionine or any special amino acid may be used. For example, in Examples which will be described later, a translation system is constructed from typical 20 amino acids except methionine and translation is started by using an initiator tRNA linked with α-N-acetylated amino acid. Such modification of the N terminal may be effective for keeping stability of the peptide. Alternatively, one of the amino acids constituting the crosslinked structure precursor may be an initiation amino acid (meaning when i is 0).

In a more typical mode of the position of the amino acids constituting a crosslinked structure precursor, these amino acids are each introduced by an elongation reaction and placed inside the peptide. This is the case where i is an integer of 1 or greater. Although no particular limitation is imposed on the size of the peptide to which the present invention is applied, the present invention is preferably used for a peptide having not greater than 25 amino acid residues and having difficulty in keeping a helix structure.

Specific examples of the compound of the formula (I) include compounds of the formula (VII):

[Chemical formula 9]

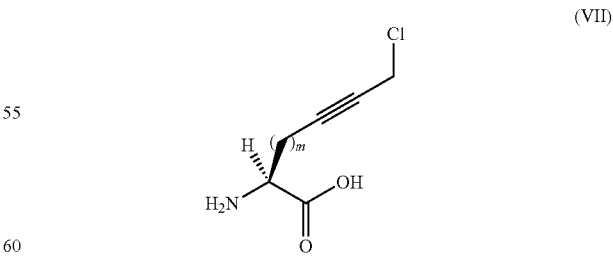

In the formula, m stands for an integer from 1 to 10. As a specific example, the compound of the formula (VII) wherein m stands for 1 can be given. This compound can be prepared at a high enantiomer excess by making use of an Schollkopf's chiral auxiliary.

Examples also include compounds of the formula (VIII):

[Chemical formula 10]

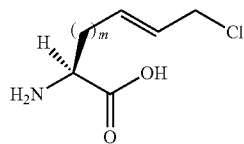

(VIII)

In the formula, m has the same meaning as described above.

Examples also include compounds of the formula (IX):

[Chemical formula 11]

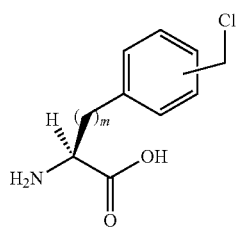

(IX)

In the formula, m stands for the same meaning as described above. As a specific example, the compound of the following formula (X) wherein m stands for 1 can be given.

[Chemical formula 12]

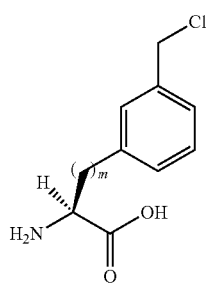

(X)

Specific examples of the compound of the formula (I) wherein (C) represents an alkyl chain include compounds represented by the formula (XI) corresponding to the formula (VII) and compounds represented by the formula (XII) corresponding to the formula (X):

[Chemical formula 13]

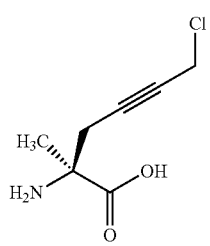

(XI)

-continued

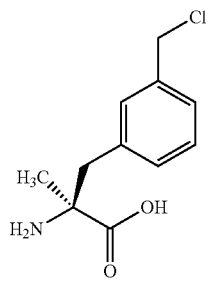

(XII)

On the other hand, specific examples of the cysteine analogue include compounds of the formula (V) or (VI).

[Chemical formula 14]

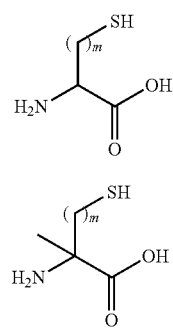

(V)

(VI)

In the formulas (V) and (VI), m has the same meaning as described above.

Additional examples include special amino acids having a sulfanyl group such as homocysteine and mercapto-norvaline.

Preparation Process of Peptide Having Crosslinked Structure Introduced Therein

Next, a preparation process of the peptide of the present invention will be described.

The peptide of the present invention can be prepared by making use of various known processes such as processes through chemical synthesis or translational synthesis or processes equivalent thereto. For example, in the chemical synthesis, a peptide containing the special amino acid of the formula (I) and the sulfanyl-containing amino acid can be synthesized by using liquid phase synthesis, solid phase synthesis using a protecting group such as Fmoc or Boc, or hybrid process using liquid phase synthesis and solid phase synthesis in combination. In the peptide thus synthesized, a thioether bond is formed spontaneously between the special amino acid of the formula (I) and the sulfanyl group without using an enzyme or the like as will be described later and a crosslinked peptide can be obtained.

As one example of the preparation process of the peptide of the present invention, a process using a cell-free translational synthesis system will next be described. In this process, a crosslinked structure is constructed by forming a covalent bond between peptide side chains by making use of a highly selective intramolecular reaction in which the special amino acid contained in the translationally synthesized peptide is involved. This process includes the following steps:

(i) a step of translationally synthesizing a special peptide having, in the molecule thereof, at least one combination of an amino acid having, in the side chain thereof, a sulfanyl group and a special amino acid represented by the formula (I); and (ii) causing, in each combination, thioether bonding between the sulfanyl group and the side chain of the special amino acid of the formula (I) to form a crosslinked structure.

The steps (i) and (ii) will hereinafter be called a translational synthesis step and a crosslinked structure formation step, respectively.

In the translational synthesis step (i), a peptide in which the following two amino acids are spaced apart with the appropriate number of amino acid residues is obtained by translational synthesis:

(a) an amino acid having, in the side chain thereof, a sulfanyl group, and (b) a special amino acid represented by the formula (I).

In the special peptide synthesized in the step (i), a chemical structure containing a combination of functional groups, that is, a sulfanyl group and a functional group of the special amino acid reactive therewith will hereinafter be called "crosslinked structure precursor". This means that a combination of the amino acids (a) and (b) in which they are spaced apart with the appropriate number of amino acid residues constitutes a crosslinked structure precursor.

For example, refer to a schematic view of FIG. 2. In FIG. 2, the combination of these amino acids is indicated by a solid black circle placed inside the peptide chain. Not only a crosslinked structure precursor combination but also a plurality of crosslinked structure precursors may be placed in one peptide chain. When a peptide chain containing a plurality of crosslinked structure precursors is synthesized by translation, a plurality of crosslinked structures can be formed in the crosslinked structure formation step (ii).

The special amino acid of the formula (I) has, as a side-chain structure permitting formation of a covalent bond for crosslinking, a structure permitting a bond formation reaction with a sulfanyl group (—SH) which is a nucleophilic functional group. As a result of this reaction, in the crosslinked structure formation step (ii), the peptide containing the crosslinked structure precursor is changed to a peptide having a crosslinked structure. In the present invention, formation of the crosslinked structure from the crosslinked structure precursor occurs spontaneously under translational synthesis conditions so that no chemical catalyst is necessary.

When the step (i) is conducted in a cell-free translation system, a peptide chain is introduced by artificially allocating the special amino acid to an existing codon by making use of genetic code reprogramming technology. More specifically, a peptide having the special amino acid introduced therein at a position designated by a codon altered (altered codon) can be obtained by preparing mRNA having a codon encoding the special amino acid and translating it under an altered genetic code table.

The term "codon" as used herein means both an altered codon and a universal codon to be used in natural translation. The altered codon is a codon which has lost its assignment to a proteinogenic amino acid and is assigned to a special amino acid by genetic code reprogramming. The special amino acid is coded only by the altered codon.

A helix peptide compound is obtained by introducing a crosslinked structure in the peptide compound thus synthesized. Although the reaction conditions for forming the crosslinked structure are determined depending on the kind of the combination of the functional groups, the reaction usually proceeds at high selectivity under the cell-free translation system conditions for synthesizing this peptide compound. Accordingly, a crosslinked peptide compound having a spontaneously formed bond can be obtained without especially controlling the reaction conditions.

Figure 3:
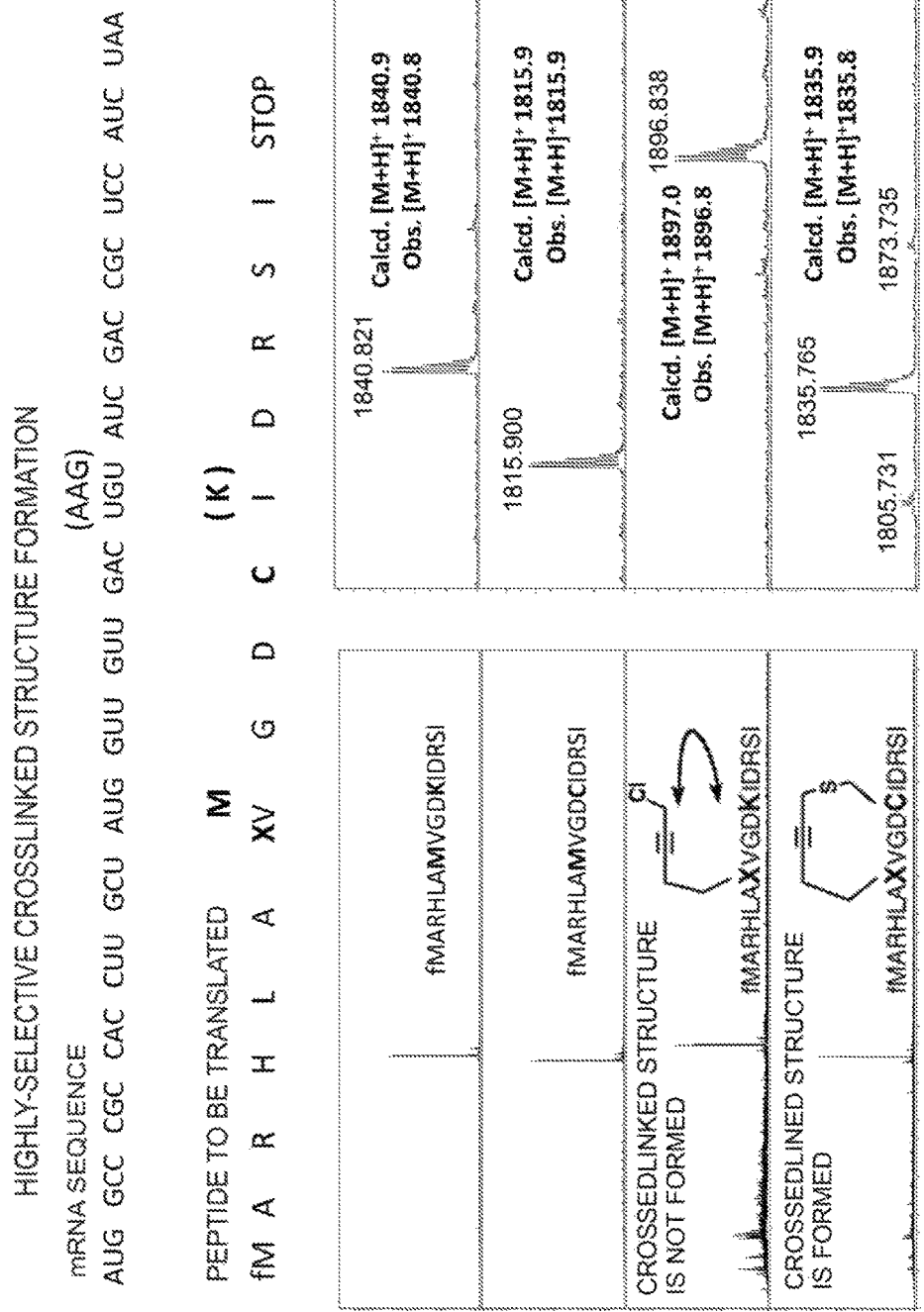
FIG. 3 shows the selective formation of a crosslinked structure.

For example, refer to FIG. 3. When peptide chains in which combinations of various amino acids introduced with an elongation codon after starting translation with formylmethionine have been placed at a positional relationship of (i,i+4), only a combination of the special amino acid X of the formula (I) and cysteine C formed a crosslinked structure through a thioether bond.

Similarly, in Examples which will be described later, described is a peptide containing a crosslinked structure precursor obtained by translational synthesis of a peptide sequence in which a special amino acid having, in the amino acid chain thereof, propargyl chloride and cysteine have been placed. In the exemplified mode, a substitution reaction by the sulfanyl group to the propargyl position spontaneously proceeds after translation to form a thioether bond and a crosslinked structure is completed.

Cell-free (In Vitro) Translation System

The term "translation system" means a place for peptide translational synthesis and it is generally a concept including both a method and a kit (substance). As the cell-free translation system to be used in the present invention, a system constructed by subdividing a known reconstituted translation system and reducing impurities as much as possible is preferably used. Specific constituents of the translation system as a kit (substance) usable in the present invention will next be described.

Specific examples of the constituents of the translation system include ribosome, IF group, EF group, RF group, RRF, a minimum set of natural amino acid, tRNA, and a specific ARS protein enzyme which will become necessary in the synthesis of an intended peptide, and energy sources for translation reaction. As the ribosome, that isolated from *Escherichia coli* and then purified is preferably used.

As the proteins, used are translation initiation factors (for example, IF1, IF2, and IF3), translation elongation factors (for example, EF-Tu, EF-Ts, and EF-G), translation termination factors (for example, RF1, RF2, RF3, and RRF), and enzymes for regeneration of an energy source (for example, creatine kinase, myokinase, pyrophosphatase, and nucleotide-diphosphatase kinase). Among them, translation termination factors and enzymes for regeneration of an energy source may be added as desired. Although T7 RNA polymerase may be added for the transcription from a template DNA, RNA polymerase is not necessary if mRNA transcribed in advance is added to the translation system.

In addition, similar to the conventional system, an appropriate buffer solution, an NTP as an energy source of a translation reaction, Creatine phosphate, and factors necessary for ribosome activation, RNA stabilization, and protein stabilization can be used as needed. While, in the typical translation reaction, N-formylmethionine is defined as initiation codon AUG by initiator tRNA so that a formyl donor such as 10-formyl-5,6,7,8-tetrahydroforlic acid (Baggott et al., 1995) is essential, in the present invention, a formyl donor is optional when a translation reaction is started with the special amino acid. For the same reason, methionyl-tRNA formyltransferase (MTF) is also not essential.

In the translation system to be used in the present invention, natural tRNAs and ARSs can be used for natural proteinogenic amino acids as in the conventional system. Natural tRNAs are, for example, a mixture obtained by collecting *Escherichia coli*, disrupting it, and purifying the tRNA fraction. They can also be commercially available. The specific A, U, C, and G in the natural tRNAs have been chemically modified with an enzyme. Alternatively, tRNAs having a natural sequence transcribed in a test tube can also be used.

On the other hand, for the special amino acid(s), not natural tRNA(s) but artificial tRNA(s), which is (are) a tRNA transcript(s) as orthogonal tRNA(s), is (are) preferably used. The artificial tRNA(s) can be prepared by in vitro transcription reaction using an appropriate RNA polymerase while using the corresponding DNA(s) as a template(s). No chemical modification can be found in such an artificial tRNA(s).

In order to introduce the special amino acid(s) into the peptide which is a translation product, orthogonal tRNA(s) acylated with the special amino acid(s) in advance is (are) added to the translation system. In a preferred mode, the tRNA(s) acylated with the special amino acid(s) is (are) prepared by binding the special amino acid(s) to the 3'-end of orthogonal tRNA(s) by using a flexizyme, under conditions free of the other tRNAs or ARSs. It is also possible to use a tRNA(s) chemically or enzymatically bound with the special amino acid(s).

Peptide Library

The term "peptide library" as used herein means a library containing two or more peptides having the above-mentioned crosslinked structure introduced therein, in other words, two or more peptides different in sequence. In the peptides constituting the peptide library, amino acid other than an amino acid having, in the side chain thereof, a sulfanyl group and a special amino acid represented by the formula (I) are arbitrary amino acids. For example, when a peptide composed of 25 amino acid residues contains only a combination of an amino acid having a sulfanyl group and a special amino acid represented by the formula (I), a peptide library contains $20^{23}$ peptides in theory even if only 20 natural amino acids are used. This means that it has a sufficient library size.

The peptide library of the present invention has a stable secondary structure due to crosslinking so that it is excellent in cell membrane permeability. Screening using this library makes it possible to obtain useful peptides such as peptides having high affinity with a target and peptides having physiological activity such as peptides inhibiting the function of a target protein.

In one mode of the peptide library, each peptide may be linked with mRNA encoding it. When they are linked, a phenotype (amino acid sequences of peptides) is displayed on a genotype (nucleic acid sequences) in the library so that it can be applied to in vitro display. In other words, a peptide is selected from a display library in which genetic information is displayed as peptides, which are translation products of it. This means that random peptide molecules in the library are attached with a tag which can be amplified or read by a molecular biological method.

In the in vitro display, peptides synthesized using a cell-free translation system (also called "in vitro translation system") are displayed while being assigned to genetic information. As this method, ribosome display, mRNA display, DNA display, and the like are known. RaPID display (not published) can also be used. Each display method has a mechanism of assigning the genetic information recorded in mRNA or DNA to a peptide encoded by the genetic information as a [genetic information]-[translation product] complex by linking them with each other. In the ribosome display, mRNA-ribosome-peptide forms a triple complex. In the mRNA display and RaPID display, an mRNA-peptide complex is formed. In DNA display, a DNA-peptide complex is formed. In the present invention, any in vitro display library can be used.

Production Process of Peptide Library

Although no particular limitation is imposed on the production process of a library of peptides having a random sequence, the library can be produced, for example, by conducting translational synthesis from a template nucleic acid (mRNA or DNA corresponding thereto) having a random sequence in a region encoding a peptide in a cell-free translation system.

Accordingly, one mode of the production method of the peptide library includes:

(i) a step of producing a library of mRNAs having, in an RNA encoding a random amino acid sequence, a combination of a codon encoding an amino acid having, in the side chain thereof, a sulfanyl group and a codon encoding a special amino acid represented by the formula (I), wherein, in each combination, the codon encoding an amino acid having, in the side chain thereof, a sulfanyl group and the codon encoding a special amino acid of the formula (i) are spaced apart with 2, 3, 6, or 10 amino acid units;

(ii) a step of translating the mRNAs by using a cell-free translation system containing a tRNA linked with the special amino acid to obtain a peptide group having a random sequence with the special amino acid placed therein; and (iii) a step of binding, in each peptide, the sulfanyl group and the side chain of the special amino acid of the formula (I) to form a crosslinked structure.

To construct a crosslinked peptide library having a random sequence, a random sequence composed of repetition of a plurality of triplets and codons encoding amino acids which will form a crosslinked structure precursor are placed in a region of an mRNA sequence encoding a peptide. For example, as shown in FIG. 5, a special amino acid having, in the side chain thereof, a propargyl chloride structure is allocated to one of elongation codons and cysteine is introduced into a position spaced apart, from the above position, by codon bases of the random sequence corresponding to the appropriate number of amino acid units (for example, 2, 3, 6, or 10 amino acid units as described above).

A template mRNA is constructed by arranging, in addition to the codons to which said two amino acids have been allocated and an initiation codon, codon bases having a random sequence with a desired length. Translation of this mRNA makes it possible to construct a thioether bond through a nucleophilic substitution reaction between propargyl chloride and the sulfanyl group located in the side chain of the cysteine and construct a crosslinked peptide library having a random sequence.

In order to construct a library having a random sequence, it is the common practice to employ NNK (N represents any base selected from G, A, C, and U and K represents U or G) as a codon sequence of mRNA which will be a template of 20 proteinogenic amino acids so that all the proteinogenic amino acids appear at random. However, when the special amino acid of the formula (I) serving as an electrophilic agent for forming a crosslinked structure is assigned to one of elongation codons, for example, AUG (AUG can be used as both of an initiation codon and an elongation codon) and a peptide library is constructed using the NNK library, AUG appears at random as one of the codons represented by NNK so that a plurality of the special amino acids is incorporated in the peptide library.

When AUG is used as the codon encoding the special amino acid of the formula (I), by way of using a repetition of triplets having NNC or NNU (N represents any one base of A, U, G, and C) as a random sequence, it is possible to avoid AUG from appearing in the random sequence. As a result, the special amino acid of the formula (I) can be introduced into only the designated position in the random sequence.

When a library of bases having an NNU or NNC random sequence is used, five amino acids (Met, Trp, Gln, Lys, and Glu) do not appear. NNK may be used in addition to NNU and NNC if the merit of causing them to appear exceeds the demerit of placing the special amino acid at a position other than the desired position.

It is also possible to use a codon corresponding to an amino acid which does not appear when NNU or NNC is used for introducing another special amino acid for forming a crosslinked structure or a special amino acid having another additional function at a designated position. For example, such a special amino acid can be introduced at a designated position by using four codons, UGG, CAG, AAG, and GAG in addition to AUG.

mRNA including NNU, NNC, and NNK can be obtained by synthesizing DNA including NNT, NNC, and NNK by using a various DNA synthesizer, followed by transcription.

In the above-mentioned illustrative mode, the special amino acid of the formula (I) is introduced through a peptide chain elongation reaction with elongator tRNA. Here, the initiator tRNA pairs with an AUG codon at a translation starting position and introduces an amino acid which is linked thereto into the peptide N-terminal. An AUG codon at the other position pairs with the elongator tRNA having a CAU codon. Two amino acids are therefore assigned to the AUG codon with two tRNAs. The AUG codon which pairs with the initiator tRNA will hereinafter be called initiation AUG and the AUG codon which pairs with the elongator tRNA will hereinafter be called AUG simply.

In the present invention, a cell-free translation system comprised of components optimized according to the intended use is used after DNA or RNA molecules corresponding to a base sequence serving as a translation template are added. A nucleic acid sequence may include, similar to a protein expression system making use of living cells, a base sequence advantageous for translation, depending on a translation system to be employed, in addition to a region encoding an intended amino acid sequence. For example, in a system using ribosome derived from *Escherichia coli*, the efficiency of a translation reaction increases when the sequence contains, upstream of the initiation codon, Shine-Dalgarno (SD) sequence, epsilon sequence, or the like.

A region encoding a peptide has, at the N terminal thereof, an initiation codon. The initiation codon is typically a triplet sequence, AUG. Using a desired sequence as an anticodon sequence in the initiator tRNA synthesized through an in vitro transcription reaction, however, enables reprogramming of the initiation codon so that another base sequence can also be used as an initiation codon in addition to AUG codon.

The region encoding a peptide has, on the C terminal side thereof, a sequence for linking a nucleic acid molecule and a peptide which is a translation product thereof for in vitro display. For example, in an mRNA display method using a puromycin linker, an mRNA library-peptide complex library is formed by adding, to a translation system, an mRNA library linked preliminarily with a puromycin linker. The linker is typically inserted between the 3' end side of the mRNA and puromycin in order to incorporate puromycin in the A site of a ribosome efficiently.

Puromycin functions as a substrate (aminoacyl tRNA analogue) of a peptide transfer reaction on the ribosome and by binding it to the C-terminal of the elongation peptide, it links between mRNA and the peptide. The mRNA display method is a technology of integrating genotype and phenotype with each other by linking an mRNA and a peptide via an appropriate linker in an in vitro translation system. Insofar as such an object is achieved, puromycin may be replaced by a linker containing another substance having a similar function, which is within a range of the recognition of those skilled in the art.

As another method, it is also possible to use a method of forming an mRNA-peptide complex library by hybridization of a linker and an mRNA in an in vitro translation system instead of the method using an mRNA linked preliminary with a linker. For example, an mRNA-peptide complex library is formed by using a phenylalanine linker (3'-phenylalanine-ACCA-PEG-[a base sequence complementary to the 3'-end region of an mRNA library]-5') prepared by using flexizyme and a strand complementary to an mRNA library in combination ("RAPID display method" described in PCT/JP2010/685459 which is an unpublished application). In this case, am mRNA contains a base sequence for hybridization with the linker downstream (3' end region) of the region encoding a peptide.

In Example which will be described specifically later, an initiation AUG codon is placed at the N terminal of a peptide, an elongation AUG codon (or codon UGC encoding Cys) encoding the special amino acid of the formula (I) is placed after a random sequence corresponding to some amino acid residues, and a codon UGC (or the above-mentioned codon encoding the special amino acid of the formula (I)) encoding Cys are placed after a random sequence of appropriate amino acid units. Then, a random sequence follows until the C terminal. Please refer to FIGS. 2 and 5. Just after it, a codon encoding GlySerGlySerGlySer serving as a linker follows.

Aminoacylation Reaction using Flexizyme

Flexizyme is an RNA catalyst (ARS ribozyme) having a function of acylating a desired tRNA with an amino acid substrate having a desired structure. Different from natural ARS protein enzymes, flexizyme has no specificity to each amino acid or each tRNA and is capable of conducting aminoacylation of a tRNA by using any amino acid other than the amino acid which is to be linked to such tRNA in nature. More specifically, it does not contain an α-substituent at the recognition site of an amino acid so that not only L amino acid but also hydroxy acid (having a hydroxyl group at the α position), α-N-methylamino acid, α-N-acylaminoacid, or D-amino acid can be used as a substrate. In addition, an amino acid modified after translation such as ε-N-acetyllysine or ε-N-methyllysine can also be used as a substrate. Details on it are described in, in addition to the above-mentioned document on flexizyme, the following documents: Y. Goto, H. Suga (2009) "Translation initiation with initiator tRNA charged with exotic peptides" Journal of the American Chemical Society, Vol. 131, No. 14, 5040-5041, WO2008/059823 "Translation and synthesis of polypeptide having nonnative structure at n-terminus and application thereof", Goto et al., ACS Chem. Biol., 2008, 3, 120-129, T. J. Kang, et al., Chem. Biol., 2008, 15, 1166-1174 "Expression of histone H3 tails with combinatorial lysine modifications under the reprogrammed genetic code for the investigation on epigenetic markers", and WO2008/117833 "Process for synthesizing cyclic peptide compound".

In the present invention, the special amino acid is introduced into a peptide sequence by adding, to a cell-free translation system, orthogonal tRNA obtained by acylation with the special amino acid by using flexizyme.

The orthogonal tRNA is a tRNA capable of efficiently expressing a designated amino acid, being paired with the codon of mRNA in a peptide synthesis reaction on a ribosome, though it is not aminoacylated in a translation system because it is not recognized by naturally occurring ARS (for example, ARS protein enzyme derived from *Escherichia coli*) inherent in the translation system. As the orthogonal tRNA, for example, a natural suppressor tRNA derived from a different species or an artificially constructed tRNA is used. As described above, an orthogonal tRNA which is an artificial transcript is preferably used for the introduction of the special amino acid in the present invention.

Flexizyme has catalytic ability with an activated amino acid ester as a substrate. It recognizes a carbonyl group which is a reaction point of an amino acid, an aromatic ring in an amino acid side chain or a leaving group, or the 5'-RCC-3' sequence portion (R represents A or G) present at the 3' end of tRNA and acylates adenosine at the 3'-end with such amino acids. Flexizyme has no specificity to the anticodon portion of tRNA. This means that even if the anticodon portion of tRNA is changed to any sequence, it has no influence on the efficiency of aminoacylation. Since any special amino acid can be linked to a tRNA having any anticodon sequence by using flexizyme, any special amino acid can be assigned to any codon. This therefore makes it possible to produce a library having any special amino acid introduced therein.

The following is a known structure of flexizyme (RNA sequence).

```
Original flexizyme Fx
                                    (SEQ ID NO: 1)
[GGAUCGAAAGAUUUCCGCAGGCCCGAAAGGGUAUUGGCGUUAGGU-3',
45 nt]

Dinitrobenzyl flexizyme dFx
                                    (SEQ ID NO: 2)
[5'-GGAUCGAAAGAUUUCCGCAUCCCCGAAAGGGUACAUGGCGUUAGG
U-3', 46 nt]

Enhanced flexizyme eFx
                                    (SEQ ID NO: 3)
[5'-GGAUCGAAAGAUUUCCGCGGCCCCGAAAGGGGAUUAGCGUUAGGU-
3', 45 nt]

Aminoflexizyme aFx
                                    (SEQ ID NO: 4)
[5'-GGAUCGAAAGAUUUCCGCACCCCCGAAAGGGGUAAGUGGCGUUAGG
U-3', 47 nt]
```

Since different from natural ARS protein enzyme, flexizyme serves as a catalyst only in a procedure of binding an amino acid substrate to tRNA while skipping a procedure of forming a high energy intermediate (aminoacyl AMP), which is the first stage of an aminoacylation reaction, it is necessary to use, as an amino acid substrate, an amino acid weakly activated in advance. This means that instead of skipping adenylation of an amino acid, an amino acid derivative having a weakly activated ester bond at a carbonyl group at which acylation proceeds is used. Activation of an acyl group is usually achieved by binding an ester having an electrophilic group to it, but an ester having a too strong electrophilic group causes not only hydrolysis in water but also acylation into a random RNA. It is therefore necessary to use a weakly activated amino acid substrate which hardly causes such a side reaction in a catalyst free state. Such weak activation can be achieved by using AMP, a cyanomethyl ester, a thioester, or a benzyl ester having an electrophilic functional group such as nitro group, fluorine, or the like.

The amino acid substrate should have, in the amino acid side chain or leaving group, an aromatic ring so as to be recognized by flexizyme. The term "activated amino acid ester" means an amino acid substrate which has, as aminoacyl AMP in a natural aminoacylation reaction, a weakly activated ester bond and at the same time, has an aromatic ring in the amino acid side chain or leaving group. Preferred examples of the activated amino acid ester include, but not limited to, aminoacyl-cyanomoethyl ester (CME: cyanomethyl ester), aminoacyl-dinitrobenzyl ester (DNB: 3,5-dinitrobenzyl ester), and aminoacyl-4-chlorobenzyl thioester (CBT: p-chloro-benzyl thioester).

For example, in Example which will be described later, α-N-acetyl-L-phenylalanine (Ac-F) is linked to an artificially constructed initiator tRNA to introduce it to the peptide N-terminal and at the same time, three amino acids (refer to the structural formula shown on the lower side of Table 1 of Example), that is, (s)-2-amino-6-chlorohexy-4-ynoic acid, (s)-2-amino-7-chlorohepto-5-ynoic acid, (s)-2-amino-8-chloroocto-6-ynoic acid, each having propargyl chloride in the side chain thereof, are linked to artificially constructed elongator tRNAs, respectively. In the case of these three compounds, (s)-2-amino-6-chlorohexy-4-ynoic acid DNB, (s)-2-amino-7-chlorohepto-5-ynoic acid DNB, and (s)-2-amino-8-chloroocto-6-ynoic acid DNB are used as substrates to mix dFx and tRNA and respective tRNAs bound to these compounds can be prepared. In the case of α-N-acetyl-L-phenylalanine, α-N-acetyl-L-phenylalanine CME is used as a substrate to mix eFx and tRNA and a tRNA bound to Nα-acetyl-L-phenylalanine can be prepared.

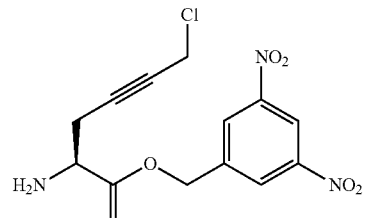

(s)-2-Amino-6-chlorohexy-4-ynoic acid DNB

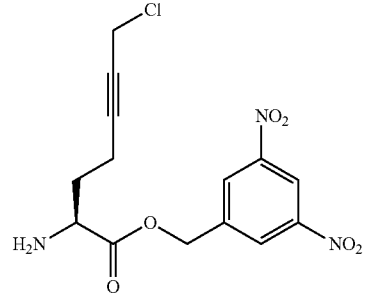

(s)-2-Amino-7-chlorohepto-5-ynoic acid DNB

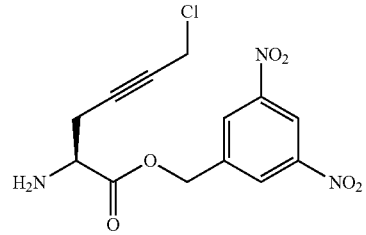

(s)-2-Amino-8-chloroocto-6-ynoic acid DNB

-continued

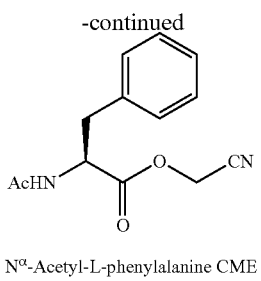

N$^\alpha$-Acetyl-L-phenylalanine CME

Acylation reaction by using flexizyme may be conducted either in a solution or in a column in which an ARS ribozyme is immobilized on a carrier. For example, when the scale of the translation reaction is as small as 100 µl or less, it is recommended to conduct acylation of tRNA in a solution by using flexizyme; dissolve pellets obtained by precipitating the reaction solution in ethanol in a proper buffer (for example, 1 mM potassium acetate, pH 5 or the like); and add the resulting solution to a translation system. As the reaction conditions, preferable conditions may be selected as needed. The following is one example of the conditions of a small-scale reaction. It is recommended to react a 0.1M reaction buffer of pH 7.5 containing from 0.5 to 20 µM tRNA, from 0.5 to 20 µM flexizyme, from 2 to 10 mM an amino acid substrate, and 0.6M $MgCl_2$, each in terms of a final concentration, at 0° C. for from 1 to 24 hours.

When the scale of the translation reaction exceeds 100 µl, it is convenient to use flexizyme immobilized on a carrier in consideration of reuse of the flexizyme. Examples of the carrier include, but not particularly limited to, resins, agarose, sepharose, and magnetic beads. With the flexizyme immobilized on the carrier, the reaction may be conducted, for example, according to the following method: Murakami, H., Bonzagni, N. J. and Suga, H. (2002), "Aminoacyl-tRNA synthesis by a resin-immobilized ribozyme", J. Am. Chem. Soc. 124(24): 6834-6835. Isolation of the aminoacylated tRNA as a reaction product can be conducted using various methods. One example is to elute it from a column with a buffer containing about 10 mM EDTA. The resin on which ARS ribozyme has been immobilized can be used in repetition a dozen times, for example, by equilibrating it with a reaction buffer.

Initiator tRNA and Elongator tRNA

It is important that in a natural translation reaction, an initiator tRNA is used only in the initiation of translation but not in an elongation reaction and on the contrary, an elongator tRNA is not used in the initiation reaction. This difference between the initiator tRNA and the elongator tRNA is also applied to the present invention.

In the present application, an artificial tRNA is preferably used for acylation of the special amino acid. A non-restrictive example of the artificial tRNA which is an elongator tRNA is tRNA$^{Asn-E2}$. The base sequence of this tRNA is based on natural tRNA$^{Asn}$ (5'-UCCUCUG$^{s4}$UAGUUCAGDCGGDAGAACGGCGGAC UQUU$^{r6}$AAYCCGUAU$^{m7}$GUCAC UGGTYCGAGUCCA-GUCAGAGGAGCCA-3') (SEQ ID NO:7) which is a tRNA for elongation reaction derived from Escherichia coli ($^{s4}$U: 4-thiouridine, D: dihydrouridine, Q: queuosine, $^{r6}$A: 6-threo-nylcarbamoyladenine, Y: wyosine, $^{m7}$G: 7-methylguanosine, T: ribothymidine). The present inventors removed modified bases from this natural tRNA and introduced mutation thereinto and thereby prepared tRNA$^{Asn-E2}$, that is, a tRNA for elongation reaction not aminoacylated with 20 amino-acylation enzymes of Escherichia coli through in vitro transcription. The NNN site corresponds to an anticodon, which is changed so as to correspond to a codon. (tRNA$^{Asn-E2}$: 5'-GGCUCUGUAGUUCAGUCGGUAGAACGGCG-GACUNNNAAUCCGUAUGUCACUGGUUCG AGUC-CAGUCAGAGCCGCCA-3' (SEQ ID NO:5) [eight positions where modifications are removed: $^{s4}$U8U, D16U, D20U, $^{r6}$A37A, Y39U, $^{m7}$G46G, T54U, and Y55U. The thirty-fourth Q is an anticodon so that it is changed so as to correspond to a codon] [mutated at four sites in total: U1G, C2G, G71C, and G72C].

A non-restrictive example of the artificial tRNA which is an initiator tRNA is tRNA$^{fMet}$. The base sequence of this tRNA is based on natural tRNA$^{fMet}$ (5'-CGCGGGG$^{s4}$UGGAGCAGCCUGGDAGCUCGUCGGG CmUCAUAACCCGAAGAUCGU CGGTYCAAAUCCG-GCCCCCGCAACCA-3') (SEQ ID NO:8) of Escherichia coli (Cm: 2'-O-methylcytidine). The present inventors removed modified bases from this natural tRNA and changed the first C of the 5' end to G and thereby prepared tRNA$^{fMet}$, that is, a tRNA for initiation reaction through in vitro transcription. The CAU site is an anticodon and corresponds to an initiation AUG codon. (tRNA$^{fMet}$ used in the present application: 5'-GGCGGGGUGGAGCAGC-CUGGUAGCUCGUCGGGCUCAUAACCCGAAGAUC-GUCG GUUCAAAUCCGGCCCCCGCAACCA-3' (SEQ ID NO:6) [six positions where modifications were removed: $^{s4}$U8U, D20U, Cm32C, T54U, Y55U] [mutated at one site: C1G]). It is important for the initiator tRNA that the first base at the 5' end (C in the natural tRNA$^{fMet}$ and G in the tRNA$^{fMet}$ of the present application) does not form a complementary strand with the seventy second base (A in the natural tRNA$^{fMet}$ and the tRNA$^{fMet}$ of the present application). This non-complementary strand transfers a formyl group to Met-tRNA$^{fMet}$, recognized by methionylformyl transferase (MTF) (with the proviso that when a special amino acid for initiation is used, it does not have any meaning) or it suppresses EF-Tu binding.

In Example which will be describe later, Nα-acetyl-L-phenylalanine is linked to tRNA$^{fMet}_{CAU}$ to introduce it into the peptide N terminal and three special amino acids having, in the side chain thereof, propargyl chloride are linked to tRNA$^{AsnE2}_{CAU}$, respectively. Although tRNA$^{AsnE2}_{NNN}$ can be used while changing the codon sequence (NNN in which N represents any base), when an altered codon encoding a special amino acid having, in the side chain thereof, a propargyl chloride structure is AUG, the anticodon sequence is CAU.

Since these initiator and elongator artificial tRNAs have orthogonality to natural ARS, a natural amino acid is not linked thereto in the translation system, but such tRNAs are accepted without a problem in the translation initiation reaction or peptide-chain elongation reaction on a ribosome. It has been confirmed in the cell-free translation system used in Example that these artificial tRNAs are usable in practice. The artificial tRNA usable in the present invention is however not limited to them. It will be apparent for those skilled in the art that tRNAs usable for introducing the special amino acid of the present invention can be selected as needed, depending on the components of the cell-free translation system to be used.

In Vitro Selection

In the present invention, the special peptide library constructed in the cell-free translation system can be completely adapted to the in vitro display technology including mRNA display so that it is possible to create peptide molecules binding to a target from the high-diversity special peptide library having $10^{13}$ or more peptides.

The in vitro display technology is utilized as a tool of directed evolution. In this directed evolution, with a view to creating proteins or peptides having a desired function or property, genes having such possibility are prepared on a large scale and a clone having a desired phenotype is selected from them. Basically, first, a DNA group (DNA library) is produced. Then, an RNA library is produced as an in vitro transcript, followed by production of a peptide group (peptide library) as an in vitro translation product. From this peptide library, peptides having a desired function or property are selected by using some screening system.

For example, when a peptide molecule binding to a certain protein is desired, a peptide group is applied in a column in which a target protein is immobilized and a mixture of the peptide molecule bound to the column can be collected. At this time, each peptide molecule is attached with a nucleic acid molecule, a template of the peptide molecule, as if a tag. In mRNA display library, each peptide molecule is attached with mRNA. Then the group of peptide-mRNA complexes thus collected is returned to DNA by using a reverse transcriptase and then amplified by using PCR to obtain a biased library containing many clones having a desired phenotype. Then, a similar selection test is conducted again.

It is also possible to conduct a reverse transcription reaction before selection in order to change the nucleic acid portion to a duplex (DNA/RNA hybrid) and thereby avoid possible collection of an RNA aptamer. By repeating this operation, a clone having a desired phenotype is concentrated in the group with the passage of the generation.

In order to identify a peptide aptamer, a gene of the peptide aptamer that binds to a target substance can be cloned by repeating a step of mixing an in vitro display library and the target substance; selecting a molecule (active species) presenting the peptide that has bound to the target substance; and producing a nucleic acid library by using PCR from the nucleic acid portion of the molecule thus selected.

As the target substance, usually any compound such as protein, peptide, nucleic acid, carbohydrate, or lipid or complex of any of them may be usable.

In order to select the active species, it is necessary to bring a [genetic information]-[peptide] complex into contact with the target substance and isolate and collect a complex that presents the peptide bound to the target substance from many other complexes that have not been bound to the target substance. Many technologies are known as such a collection method.

For example, it is convenient to give the target substance some modifications which can be collected by binding to a solid phase. For example, a polyhistidine tag linked to the target substance can be collected by using specific binding of the polyhistidine tag to a carrier having Ni-NTA supported thereon. Examples of such a specific binding usable include a combination of polyhistidine peptide/metal ion (nickel, cobalt, etc.), biotin-binding protein (avidin, streptavidin, etc.)/biotin, maltose-binding protein/maltose, glutathione-S-transferase/glutathione, and antibody/antigen (epitope) combinations, but specific binding is not limited to them.

The present invention includes creating a special peptide that binds to a target substance by repeating in vitro selection having the following steps: bringing a peptide library to a target substance, selecting an active species presenting the peptide that has bound to the target substance, amplifying the nucleic acid sequence of the thus-selected active species, and selecting an active species from the peptide library synthesized again in a cell-free translation system with the amplified nucleic acid sequence as a template. In particular, by using a library containing secondary structure-directing peptides, that is, a library intended to have many predetermined secondary structures, that is, helix structures by incorporating a crosslinked structure in a linear peptide, a three-dimensional structure suited for intermolecular interaction is provided so that it is possible not only to obtain molecules that easily bind to the target protein but also to acquire peptides that bind to a site involved in the intermolecular interaction of the protein and show inhibitory activity.

Creation of a special peptide compound that binds to a target substance includes collecting active species presenting peptides that have bound to the target substance to analyze their nucleic acid sequence, determining a peptide sequence from the nucleic acid sequence, selecting appropriate special peptides based on the resulting peptide sequence, and obtaining an amino acid sequence and a nucleic acid sequence of the special peptides that bind to the target substance. Moreover, based on the sequence information thus obtained, a special peptide can be synthesized, purified, and isolated by using a desired method. From the special peptide thus obtained, a special peptide having higher activity can be obtained by evaluating the binding ability to a target protein or confirming the inhibitory activity against the target protein.

Accordingly, the present invention includes a method of obtaining a peptide having inhibitory activity against intermolecular interaction of a target protein from a peptide library, including:

(i) a primary screening stage of selecting a peptide that binds to a target protein, and (ii) a secondary screening stage of evaluating the binding ability of the peptide selected in the primary screening stage and determining that the peptide shows a definite binding force;

the primary screening stage includes:

(a) producing a secondary-structure-directing peptide library, (b) bringing the peptide library into contact with a target protein; and (c) selecting a peptide molecule that binds to the target protein.

Construction Method of Helix-containing Library when Bcl-2 is a Target and Method of Acquiring Therefrom Peptides Inhibiting Intermolecular Interaction A description will hereinafter be made on the construction method of a peptide library when Bcl-2 is used as a target protein and a method of acquiring therefrom inhibitory peptides (FIG. 4). This target protein will be addressed later in the section of Example. The mode described here is exemplary only and the present invention is not limited to it.

Target Protein Bcl-2

Apoptosis which is programmed cell death occurs through various pathways and one of them is a control mechanism in which Bcl-2 protein is involved. Bcl-2 protein binds to a protein that induces apoptosis and thereby suppresses its activity. It is known that in cancer cells, much Bcl-2 protein is expressed and prevents apoptosis from being induced.

If molecules that bind strongly to Bcl-2 at high sensitivity can be obtained, they will inhibit Bcl-2 from binding to an apoptosis-inducing protein and thereby introduce apoptosis to cancer cells. Such inhibitory molecules have recently been studied energetically, but it has been difficult to develop such a molecule inhibiting interaction between proteins. A helix structure called "BH3 domain" contained in the Bcl-2 protein is used for this intermolecular interaction so that it is presumed to be possible to obtain a highly-selective and strong inhibitor if a library of molecules having a helix structure is formed. Based on this presumption, molecules have been searched from a chemical library of the above-described peptides having a crosslinked structure formed through alkene formation, but molecules having strong inhibitory activity have not yet been obtained.

Construction of mRNA Library

First, in order to construct a peptide library through translation, an mRNA library serving as a template is produced. The length of the sequence of a portion of the mRNA to be translated is not limited. For example, it can be a length including from 16 to 24 codons (for example, pools from 16-1 to 24-4 in FIG. 5). In these codons, that at the N-terminal is an initiation AUG codon. A codon encoding GlySerGlySerGlySer which will be a linker may be added to the C-terminal side. The initiation AUG codon may have, downstream thereof, a random codon sequence of NNU or NNC (N represents any one base of A, U, G, and C). In this random sequence, as a specific one codon, an AUG codon is placed for introducing the special amino acid of the formula (I) and at a position separated by 2, 3, 6, or 10 amino acid units from it, a codon UGC encoding Cys is placed (for example, FIGS. 2 and 5).

Construction of Peptide Library

The mRNA library is translated under an altered genetic code table. For example, a translation system is constructed by removing methionine from typical 20 amino acids and a template mRNA is translated by using, instead of methionine, (i) tRNA$^{fMet}_{CAU}$ to which α-N-acetylated amino acid has been linked and (ii) tRNA$^{AsnE2}_{CAU}$ to which a special amino acid having, in the side chain thereof, a propargyl chloride structure has been linked. These two aminoacyl tRNAs can be prepared by using flexizyme.

Here, the aminoacyl tRNA (i) is recognized by an initiation factor and matches with an initiation AUG codon, while the aminoacyl tRNA (ii) is recognized by an elongation factor and matches with an AUG codon. It is therefore possible to introduce two amino acids into an AUG codon only by removing methionine. In the translated peptide, a crosslinked structure is formed through a thioether bond obtained by the action of the sulfanyl group of cysteine on the propargyl chloride structure.

Moreover, by binding puromycin to the 3'-end of each mRNA of the mRNA library in advance, the C terminal of the peptide is linked to mRNA via Pu (puromycin) after translation. For initiation, any special amino acids other than N$^α$-acetyl-L-phenylalanine, methionine, or other 19 proteinogenic amino acids may be used.

Acquisition of Inhibitory Peptide

The peptide library thus obtained is screened by various in vitro display methods such as mRNA display method and ribosome display method and peptides that bind to Bcl-2 are selected.

Since a secondary structure-directing peptide library designed so that a helix structure such as BH3 domain that interacts with a target protein is formed stably in a translated peptide is used, even if screening is conducted with only binding as an indicator, there is a high possibility of the peptide thus obtained binding to a molecular recognition site of the target protein and inhibiting its intermolecular interaction.

Construction of Peptide Library Against Different Target

The present invention is used for screening with various molecules including Bcl-2 as a target. As the target molecule, those exerting intermolecular interaction by recognizing a helix structure are preferably selected. Examples of the molecule that exerts intermolecular interaction by recognizing a helix structure include, but not limited to, p53 and hDM2 (F. Bernal, A. F. Tyler, S. J. Korsmeyer, L. D. Walensky, G. L. Verdine J. Am. Chem. Soc. 129 2456-2457 (2007)).

The present invention will hereinafter be described specifically. These examples are exemplary only and are not intended to limit the scope of the invention.

Example

In order to obtain a peptide that binds to the site of intermolecular interaction by the BH3 domain of Bcl-2 and thereby inhibits its intermolecular interaction, a peptide library (NNU mRNA library) having, in the sequence thereof, a crosslinked structure formed by a special amino acid and cysteine was constructed, followed by selection using the mRNA display method.

NNU mRNA Library

First, a double-stranded DNA having the following sequence was prepared (in the following sequence, only a Forward strand is described in the order of 5'→3').

```
                                        (SEQ ID NO: 9)
TAATACGACTCACTATAGGGTTAACTTTAAGAAGGAGATATACAT(ATG)
(NNT)s(ATG)(NNT)3(TGC)(NNT)t(GGT)(AGC)(GGC)(AGC)
(GGC)(AGC)(TAG)GACGGGGGCGGAAA
```

With regard to the translation region, one codon is shown in parentheses; N represents any one of A, T, G, and C; s and t stand for the repetition number of the triplet and correspond to 2 and 8, 6 and 4, 2 and 12, 6 and 8, 10 and 4, 2 and 16, 6 and 12, 10 and 8, or 14 and 4, respectively.

Then, it was transcribed by using T7 RNA polymerase to obtain a library composed of mRNA pools represented by the following sequence (refer to the table shown on the lower side of FIG. 5).

```
                                       (SEQ ID NO: 10)
GGGUUAACUUUAAGAAGGAGAUAUACAU(AUG)(NNU)s(AUG)
(NNU)3(UGC)(NNU)t(GGU)(AGC)(GGC)(AGC)(GGC)
(AGC)(UAG)GACGGGGGCGGAAA
```

The transcripts thus obtained were mixed in equal amount and provided for the following test.

mRNA Display

Peptides that bound to Bcl-2 were selected from a random peptide library by repeating the cycle from "linking with a puromycin linker" to "amplification of sequence information of collected peptides" (FIG. 4).

Linking with Puromycin Linker

The puromycin linker having the below-described sequence was annealed with the above-mentioned mRNA library and linked via T4 RNA Ligase. SPC18 represents PEG having C and O in total of 18.

```
                                        (SEQ ID NO: 11)
         pdCTCCCGCCCCCCGTCC(SPC18)5CC(Pu)
```

Translation

The mRNA linked with the linker was translated using the mRNA-altered genetic code table (FIG. 6). In this Example, a translation system was constructed by removing methionine from typical 20 amino acids and then, the following two aminoacyl tRNAs (i) and (ii):

(i) tRNA$^{fMet}_{CAU}$ to which α-N-acetyl-L-phenylalanine had been linked, and (ii) tRNA$^{AsnE2}{}_{CAU}$ to which (s)-2-amino-6-chlorohexy-4-ynoic acid ($X_0$), (s)-2-amino-7-chlorohepto-5-ynoic acid ($X_1$), and (s)-2-amino-8-chloroocto-6-ynoic acid ($X_2$) had been added respectively, each prepared using flexizyme were added. Translation was conducted using the resulting translation system.

Subsequent to the translation, a thioether bond was formed between the propargyl chloride structure contained in these special amino acids and the sulfanyl group of cysteine. Thus, a crosslinked peptide library was synthesized and a complex in which mRNA had bound to the C terminal of the peptide via Pu was constructed.

Acquisition of Peptide that Binds to Bcl-2

The crosslinked peptide library thus produced was mixed with Bcl-2 immobilized on TALON beads, followed by stirring at 4° C. for 30 minutes. The supernatant was removed by using a magnet and the remaining magnetic particles were washed with a buffer. A PCR solution was added to the beads and the resulting mixture was heated at 95° C. for 5 minutes. The peptide was extracted from the beads and the supernatant was collected.

Amplification of Sequence Information of Peptide thus Collected

The peptide-mRNA bound to Bcl-2 thus collected was amplified as DNA by reverse transcription•PCR. The DNA thus obtained was transcribed into mRNA.

Identification of Peptide Sequence thus Selected

When the recovery of the peptide-mRNA became saturated after repeating the above-mentioned series of operations, TA cloning was conducted with amplified DNA and the peptide sequence thus obtained was identified.

Results

When the NNU mRNA library is translated, an AUG codon in the random sequence is translated into a special amino acid molecule having in the side chain thereof propargyl chloride and a covalent bond is formed with the sulfanyl group of cysteine coded at a position four amino acid units away from it. Thus, a crosslinked peptide library is formed. When mRNA display was conducted using this peptide library, the recovery of the mRNA became saturated on the seventh round in the peptide library using any of the following three special amino acids different in linker length between propargyl chloride and the amino acid main chain structure: (s)-2-amino-6-chlorohexy-4-ynoic acid ($X_0$), (s)-2-amino-7-chlorohepto-5-ynoic acid ($X_1$), (s)-2-amino-8-chloroocto-6-ynoic acid($X_2$).

As a result of identification of the peptide sequence after the sixth round, it has been found that most of the sequences had a crosslinked structure and peptides having two aspartic acids near the center of sequence were obtained (Table 1). The concentrated peptide sequences have two aspartic acids in common, which suggests that a molecule inhibiting the interaction with Bcl-2 can be obtained as expected by using the mRNA display method.

TABLE 1

| | | | | |
|---|---|---|---|---|
| A-1 | Ac—FPHX$_0$TIACRADSYDSYVRLAATFL | | B-1 | Ac—FPNNRLAYAADLYDAX$_1$RALCNPTT |
| A-2 | Ac—FPHX$_0$TIACRADSYDSYVRLVATFR | | B-4 | Ac—FDSX$_1$TYRCYADIFDAHVRLVHALD |
| A-3 | Ac—FLNRHNNAYYTX$_0$GYACLGRLYRLL | | B-5 | Ac—FDTYRYAFIADSHDAX$_1$HTICNTRY |
| A-4 | Ac—FFNRHNNAYYTX$_0$GYACLGRLYRLL | | B-6 | Ac—FDTYRYAFIADSHDAX$_1$HTICNTRH |
| A-5 | Ac—FIIX$_0$RFSCLADSYDASRHIF | | B-7 | Ac—FTDX$_1$LIYCADSYDAHIRIARYLHF |
| C-1 | Ac—FTFX$_2$PLICRADDFDAIRILRGIVN | | B-8 | Ac—FFAHRADLYDAX$_1$RRICSARP |
| C-2 | Ac—FDHNRYRALADIDNAX$_2$RILCARVL | | B-9 | Ac—FRRFAYRSDLHDAYIX$_1$FRRCINRH |

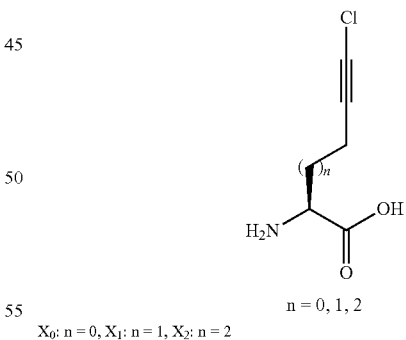

$n = 0, 1, 2$
$X_0: n = 0, X_1: n = 1, X_2: n = 2$

The amino acid sequences of A-1 to A-5, B-1 to B-9, and C-1 to C-2 are set forth as SEQ ID Nos:12 to 25 in the Sequence Listing, respectively.

From the above results, it has been confirmed that the in vitro display functions effectively by using a peptide having a crosslinked peptide structure.

Evaluation of Binding Ability of Selected Peptide to Bcl-2

Next, a crosslinked peptide having the amino acid sequence as shown in the above table was synthesized by using a Fmoc solid-phase method and its binding ability was evaluated by calculating a dissociation constant (KD) in accordance with an evaluation method using SPR (Surface Plasmon Resonance).

Described specifically, first, a solution containing $NiCl_2$ was applied on a substrate to which Ni could be bound and then Bcl-2 protein having His tag on the C terminal side thereof was applied to immobilize the protein on the substrate. Then, a solution containing a solid-phase synthesized peptide was added successively while appropriately changing the concentration. During addition, a change in refractive index depending on the weight on the substrate was read and bond strength was evaluated based on the binding rate and dissociation rate of the peptide calculated. The results are shown in the following table.

TABLE 5

| | | KD (nM) |
|---|---|---|
| A-1 | Ac—FPHX$_0$TIACRADSYDSYVRLAATFL—NH$_2$ | 0.37 |
| A-1A | Ac—FPHA TIAARADSYDSYVRLAATFL—NH$_2$ | 15 |
| A-2 | Ac—FPHX$_0$TIACADSYDSYVRLVATFR—NH$_2$ | 0.14 |
| A-2A | Ac—FPHA TIAARADSYDSYVRLVATFR—NH$_2$ | 3.6 |
| A-3 | Ac—FLNRHNNAYYTX$_0$GYACLGRLYRLL—NH$_2$ | >0.1 |

TABLE 5-continued

| | | KD (nM) |
|---|---|---|
| A-3A | Ac—FLNRHNNAYYTA GYAALGRLYRLL—NH$_2$ | Unmeasured |
| A-4 | Ac—FFNRHNNAYYTX$_0$GYACLGRLYRLL—NH$_2$ | >0.1 |
| A-4A | Ac—FFNRHNNAYYTA GYAALGRLYRLL—NH$_2$ | ~14 |
| A-5 | Ac—FIIX$_0$RFSCLADSYDASRHIF—NH$_2$ | 0.17 |
| A-5A | Ac—FIIA RFSALADSYDASRHIF—NH$_2$ | 0.58 |

The amino acid sequences of A-1A to A-4A are set forth as SEQ ID Nos:26 to 30 in the Sequence Listing, respectively.

It has been found that all the peptides thus synthesized had a dissociation constant (KD) less than 1 nM and thus showed strong binding ability.

[Sequence Listing Free Text]
SEQ ID NO:1: flexizyme Fx
SEQ ID NO:2: dinitrobenzylflexizyme dFx
SEQ ID NO:3: enhanced flexizyme eFx
SEQ ID NO:4: aminoflexizyme aFx
SEQ ID NO:5: tRNA$^{AsnE2}$
SEQ ID NO:6: tRNA$^{fMet}$
SEQ ID NO:7: tRNA$^{Asn}$ of *Escherichia coli*
SEQ ID NO:8: tRNA$^{fMet}$ of *Escherichia coli*

The invention claimed is:

1. A peptide having a secondary structure stabilized by a crosslinked structure, comprising at least one combination of a special amino acid represented by the following formula (I):

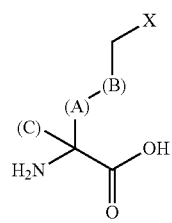

(I)

wherein (A) represents a single bond or a linking group having, in the main chain thereof, from 1 to 10 atoms, (B) represents a group containing at least one carbon-carbon double bond, a group containing at least an aromatic ring, or a ketone group, (C) represents a hydrogen atom or an alkyl group which may be substituted with a substituent, and X represents a group substitutable by a substitution reaction with a sulfanyl group, and an amino acid having, in the side chain thereof, a sulfanyl group; and having the crosslinked structure formed through a thioether bond between the side chain of the special amino acid residue and the sulfanyl group.

2. The peptide according to claim 1, wherein in the formula (I), (A) is selected from the class consisting of a single bond, alkylene groups having from 1 to 10 carbon atoms, alkenylene groups having from 2 to 10 carbon atoms, and alkynylene groups having from 2 to 10 carbon atoms, which may be substituted with a substituent; and alkylene groups, alkenylene groups, and alkynylene groups having, in the main chain thereof, 10 or less atoms, in which one or two carbon atoms in the main chain have been substituted with an oxygen atom, a nitrogen atom, or a sulfur atom and which may be substituted with a substituent, (B) is selected from the class consisting of —C═C—, —Ar—, —Ar—Ar—, —Ar—C≡C—, —Ar—C═C—, —Ar—NHC(O)—, and —Ar—C(O)—, (C) is selected from the class consisting of hydrogen, a methyl group, an ethyl group, a propyl group, a butyl group, and a pentyl group, and X is selected from the class consisting of Cl, Br, I, —OSO₂Me, a tosyl group, a nosyl group, and —OSO₂—Ar—R, wherein, R represents a group selected from the class consisting of CH₃, NO₂, CF₃, and H.

3. The peptide according to claim 1, wherein the special amino acid of the formula (I) is represented by formula (III) or formula (IV):

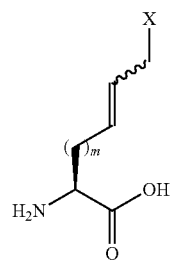

(III)

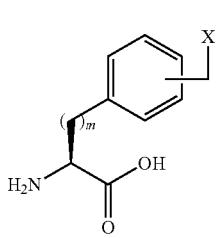

(IV)

wherein m represents an integer selected from 1 to 10 and selected from the group consisting of Cl, Br, I, —OSO₂Me, a tosyl group, a nosyl group, and —OSO₂—Ar—R wherein, R represents a group selected from the class consisting of CH₃, NO₂, CF₃ and H.

4. The peptide according to claim 1, wherein the amino acid having a sulfanyl group is selected from the group consisting of cysteine and cysteine analogues represented by the following formulas (V) and (VI):

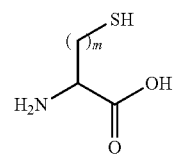

(V)

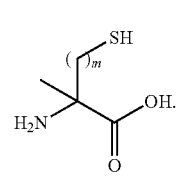

(VI)

5. The peptide according to claim 1, wherein the special amino acid residue and the amino acid residue having, in the side chain thereof, a sulfanyl group are, in each combination, placed with 2, 3, 6, or 10 amino acid residues therebetween.

6. A peptide library comprising two or more kinds of the peptide as claimed in claim 1.

7. The peptide library according to claim 6, wherein each of the peptides is linked to an mRNA encoding the peptide.

8. A method of constructing the peptide library as claimed in claim 6, comprising:

(i) producing an mRNA library which contains at least one combination of a codon encoding an amino acid having, in the side chain thereof, a sulfanyl group and a codon encoding the special amino acid represented by the formula (I)

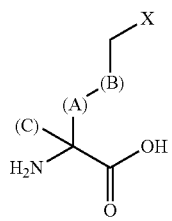

(I)

wherein (A) represents a single bond or a linking group having, in the main chain thereof, from 1 to 10 atoms, (B) represents a group containing at least one carbon-carbon double bond, a group containing at least an aromatic ring, or a ketone group, (C) represents a hydrogen atom or an alkyl group which may be substituted with a substituent, and X represents a group substitutable by a substitution reaction with a sulfanyl group, in an RNA encoding a random amino acid sequence; in each combination, the codon encoding an amino acid having, in the side chain thereof, a sulfanyl group and the codon encoding the special amino acid of the formula (I) being placed with 2, 3, 6, or 10 amino acid units therebetween; and (ii) translating the mRNA by using a cell-free translation system containing a tRNA to which the special amino acid has been linked and thereby obtaining a group of peptides having the special amino acid placed in the random sequence; and (iii) forming, in each of the peptides, a crosslinked structure by binding the sulfanyl group to the side chain of the special amino acid of the formula (I).

9. A method of constructing the peptide library as claimed in claim 8, comprising:

in step (i), binding puromycin to the 3'-end of the mRNA to obtain a puromycin-bound mRNA library;

in the step (ii), causing the puromycin-bound mRNA library to express in a cell-free translation system to obtain a peptide-mRNA complex having the special amino acid placed in the random sequence; and conducting the step (iii).

10. The method according to claim 8, wherein an altered codon encoding the special amino acid of the formula (I) is AUG codon and the mRNA random sequence is composed of repetition of a triplet of either one of an NNC or NNU sequence, wherein N represents any one base of A, U, G, and C.

11. A method of selecting a peptide that binds to a target protein from the peptide library as claimed in claim 6, comprising:

(i) bringing the peptide library into contact with the target protein, followed by incubation; and (ii) selecting a peptide molecule that binds to the target protein.

12. A method of selecting, from the peptide library as claimed in claim 11, a peptide having inhibitory activity against the intermolecular interaction of a target protein, comprising:

(i) primary screening, including the steps (i) and (ii), for selecting a peptide that binds to the target protein; and (ii) secondary screening for evaluating inhibitory activity of the peptide, which has been selected in the primary screening (i), against intermolecular interaction of the target protein and thereby determining that the peptide has inhibitory activity against the intermolecular interaction of the target protein.

13. A process of preparing a peptide that binds to a target protein:

(i) bringing the peptide library as claimed in claim 7 into contact with the target protein while incubating;

(ii) selecting a peptide-mRNA complex that binds to the target protein;

(iii) amplifying the mRNA of the selected peptide-mRNA complex to obtain a peptide-mRNA complex;

(iv) repeating the steps (i) to (iii) at least once to concentrate the peptide-mRNA complex having high-affinity; and (v) causing the mRNA of the peptide-mRNA complex concentrated in the step (iv) to express the peptide.

14. The method according to claim 11, wherein the target protein is a molecule that suppresses apoptosis.

15. A special amino acid represented by the following formula (I);

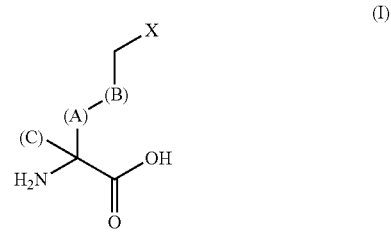

(I)

wherein (A) represents a single bond or a linking group having, in the main chain thereof, from 1 to 10 atoms, (B) represents a group containing at least one carbon-carbon double bond, or a group containing at least an aromatic ring, or a ketone group; (C) represents a hydrogen atom or an alkyl group having from 1 to 3 carbon atoms which may be substituted with a substituent; and X represents a group substitutable by a substitution reaction with a sulfanyl group.

* * * * *

SEQUENCE LISTING

```
<160> NUMBER OF SEQ ID NOS: 45

<210> SEQ ID NO 1
<211> LENGTH: 45
<212> TYPE: RNA
<213> ORGANISM: Artificial Sequence
<220> FEATURE:
<223> OTHER INFORMATION: Nucleic acid sequence of Flexizyme, Fx

<400> SEQUENCE: 1
ggaucgaaag auuuccgcag gcccgaaagg guauuggcgu uaggu            45

<210> SEQ ID NO 2
<211> LENGTH: 46
<212> TYPE: RNA
<213> ORGANISM: Artificial Sequence
<220> FEATURE:
<223> OTHER INFORMATION: Nucleic acid sequence of dinitrobenzyl-
      Flexizyme, dFx

<400> SEQUENCE: 2
ggaucgaaag auuuccgcau ccccgaaagg guacauggcg uuaggu           46

<210> SEQ ID NO 3
<211> LENGTH: 45
<212> TYPE: RNA
<213> ORGANISM: Artificial Sequence
<220> FEATURE:
<223> OTHER INFORMATION: Nucleic acid sequence of enhanced Flexizyme,
      eFx

<400> SEQUENCE: 3
```

```
ggaucgaaag auuccgcgg ccccgaaagg ggauuagcgu uaggu            45
```

<210> SEQ ID NO 4
<211> LENGTH: 47
<212> TYPE: RNA
<213> ORGANISM: Artificial Sequence
<220> FEATURE:
<223> OTHER INFORMATION: Nucleic acid sequence of amino-Flexizyme, aFx

<400> SEQUENCE: 4

```
ggaucgaaag auuccgcac ccccgaaagg gguaaguggc guuaggu          47
```

<210> SEQ ID NO 5
<211> LENGTH: 76
<212> TYPE: RNA
<213> ORGANISM: Artificial Sequence
<220> FEATURE:
<223> OTHER INFORMATION: Nucleic acid sequence of tRNA Asn-E2
<220> FEATURE:
<221> NAME/KEY: tRNA
<222> LOCATION: (34)..(36)
<223> OTHER INFORMATION: Anticodon
<220> FEATURE:
<221> NAME/KEY: misc_feature
<222> LOCATION: (34)..(36)
<223> OTHER INFORMATION: n is any base

<400> SEQUENCE: 5

```
ggcucuguag uucagucggu agaacggcgg acunnnaauc cguaugucac ugguucgagu   60
ccagucagag ccgcca                                                  76
```

<210> SEQ ID NO 6
<211> LENGTH: 77
<212> TYPE: RNA
<213> ORGANISM: Artificial Sequence
<220> FEATURE:
<223> OTHER INFORMATION: Nucleic acid sequence of Artificial tRNA fMet

<400> SEQUENCE: 6

```
ggcggggugg agcagccugg uagcucgucg ggcucauaac ccgaagaucg ucgguucaaa   60
uccggccccc gcaacca                                                 77
```

<210> SEQ ID NO 7
<211> LENGTH: 76
<212> TYPE: RNA
<213> ORGANISM: Escherichia coli
<220> FEATURE:
<221> NAME/KEY: misc_feature
<223> OTHER INFORMATION: Nucleic acid sequence of tRNA Asn
<220> FEATURE:
<221> NAME/KEY: modified_base
<222> LOCATION: (8)..(8)
<223> OTHER INFORMATION: s4u
<220> FEATURE:
<221> NAME/KEY: misc_feature
<222> LOCATION: (34)..(34)
<223> OTHER INFORMATION: n is queuosine
<220> FEATURE:
<221> NAME/KEY: modified_base
<222> LOCATION: (37)..(37)
<223> OTHER INFORMATION: t6a
<220> FEATURE:
<221> NAME/KEY: modified_base
<222> LOCATION: (46)..(46)
<223> OTHER INFORMATION: m7g
<220> FEATURE:
<221> NAME/KEY: misc_feature
<222> LOCATION: (54)..(54)
<223> OTHER INFORMATION: n is ribothymidine

<400> SEQUENCE: 7
uccucuguag uucagdcggd agaacggcgg acunuuaayc cguaugucac uggnycgagu    60
ccagucagag gagcca                                                    76

<210> SEQ ID NO 8
<211> LENGTH: 77
<212> TYPE: RNA
<213> ORGANISM: Escherichia coli
<220> FEATURE:
<221> NAME/KEY: misc_feature
<223> OTHER INFORMATION: Nucleic acid sequence of tRNA fMet
<220> FEATURE:
<221> NAME/KEY: modified_base
<222> LOCATION: (8)..(8)
<223> OTHER INFORMATION: s4u
<220> FEATURE:
<221> NAME/KEY: modified_base
<222> LOCATION: (33)..(33)
<223> OTHER INFORMATION: 2'-O-methylcytidine
<220> FEATURE:
<221> NAME/KEY: misc_feature
<222> LOCATION: (55)..(55)
<223> OTHER INFORMATION: n is ribothymidine

<400> SEQUENCE: 8
cgcggggugg agcagccugg dagcucgucg ggcucauaac ccgaagaucg ucggnycaaa    60
uccggccccc gcaacca                                                   77

<210> SEQ ID NO 9
<211> LENGTH: 189
<212> TYPE: DNA
<213> ORGANISM: Artificial Sequence
<220> FEATURE:
<223> OTHER INFORMATION: Nucleic acid sequence of DNA template for NNU
      mRNA Library
<220> FEATURE:
<221> NAME/KEY: misc_feature
<222> LOCATION: (49)..(50)
<223> OTHER INFORMATION: n stands for a, t, g or c.
<220> FEATURE:
<221> NAME/KEY: misc_feature
<222> LOCATION: (52)..(53)
<223> OTHER INFORMATION: n stands for a, t, g or c.
<220> FEATURE:
<221> NAME/KEY: misc_feature
<222> LOCATION: (55)..(56)
<223> OTHER INFORMATION: n may be present or absent, and if present n
      stands for a, t, g, or c.
<220> FEATURE:
<221> NAME/KEY: misc_feature
<222> LOCATION: (57)..(57)
<223> OTHER INFORMATION: n may be present or absent, and if present n
      stands for t.
<220> FEATURE:
<221> NAME/KEY: misc_feature
<222> LOCATION: (58)..(59)
<223> OTHER INFORMATION: n may be present or absent, and if present n
      stands for a, t, g, or c.
<220> FEATURE:
<221> NAME/KEY: misc_feature
<222> LOCATION: (60)..(60)
<223> OTHER INFORMATION: n may be present or absent, and if present n
      stands for t.
<220> FEATURE:
<221> NAME/KEY: misc_feature
<222> LOCATION: (61)..(62)
<223> OTHER INFORMATION: n may be present or absent, and if present n
      stands for a, t, g, or c.
<220> FEATURE:
<221> NAME/KEY: misc_feature
<222> LOCATION: (63)..(63)
<223> OTHER INFORMATION: n may be present or absent, and if present n
      stands for t.

-continued

```
<220> FEATURE:
<221> NAME/KEY: misc_feature
<222> LOCATION: (64)..(65)
<223> OTHER INFORMATION: n may be present or absent, and if present n
      stands for a, t, g, or c.
<220> FEATURE:
<221> NAME/KEY: misc_feature
<222> LOCATION: (66)..(66)
<223> OTHER INFORMATION: n may be present or absent, and if present n
      stands for t.
<220> FEATURE:
<221> NAME/KEY: misc_feature
<222> LOCATION: (67)..(68)
<223> OTHER INFORMATION: n may be present or absent, and if present n
      stands for a, t, g, or c.
<220> FEATURE:
<221> NAME/KEY: misc_feature
<222> LOCATION: (69)..(69)
<223> OTHER INFORMATION: n may be present or absent, and if present n
      stands for t.
<220> FEATURE:
<221> NAME/KEY: misc_feature
<222> LOCATION: (70)..(71)
<223> OTHER INFORMATION: n may be present or absent, and if present n
      stands for a, t, g, or c.
<220> FEATURE:
<221> NAME/KEY: misc_feature
<222> LOCATION: (72)..(72)
<223> OTHER INFORMATION: n may be present or absent, and if present n
      stands for t.
<220> FEATURE:
<221> NAME/KEY: misc_feature
<222> LOCATION: (73)..(74)
<223> OTHER INFORMATION: n may be present or absent, and if present n
      stands for a, t, g, or c.
<220> FEATURE:
<221> NAME/KEY: misc_feature
<222> LOCATION: (75)..(75)
<223> OTHER INFORMATION: n may be present or absent, and if present n
      stands for t.
<220> FEATURE:
<221> NAME/KEY: misc_feature
<222> LOCATION: (76)..(77)
<223> OTHER INFORMATION: n may be present or absent, and if present n
      stands for a, t, g, or c.
<220> FEATURE:
<221> NAME/KEY: misc_feature
<222> LOCATION: (78)..(78)
<223> OTHER INFORMATION: n may be present or absent, and if present n
      stands for t.
<220> FEATURE:
<221> NAME/KEY: misc_feature
<222> LOCATION: (79)..(80)
<223> OTHER INFORMATION: n may be present or absent, and if present n
      stands for a, t, g, or c.
<220> FEATURE:
<221> NAME/KEY: misc_feature
<222> LOCATION: (81)..(81)
<223> OTHER INFORMATION: n may be present or absent, and if present n
      stands for t.
<220> FEATURE:
<221> NAME/KEY: misc_feature
<222> LOCATION: (82)..(83)
<223> OTHER INFORMATION: n may be present or absent, and if present n
      stands for a, t, g, or c.
<220> FEATURE:
<221> NAME/KEY: misc_feature
<222> LOCATION: (84)..(84)
<223> OTHER INFORMATION: n may be present or absent, and if present n
      stands for t.
<220> FEATURE:
<221> NAME/KEY: misc_feature
<222> LOCATION: (85)..(86)
<223> OTHER INFORMATION: n may be present or absent, and if present n
      stands for a, t, g, or c.
<220> FEATURE:
<221> NAME/KEY: misc_feature
<222> LOCATION: (87)..(87)
<223> OTHER INFORMATION: n may be present or absent, and if present n
```

```
      stands for t.
<220> FEATURE:
<221> NAME/KEY: misc_feature
<222> LOCATION: (88)..(89)
<223> OTHER INFORMATION: n may be present or absent, and if present n
      stands for a, t, g, or c.
<220> FEATURE:
<221> NAME/KEY: misc_feature
<222> LOCATION: (90)..(90)
<223> OTHER INFORMATION: n may be present or absent, and if present n
      stands for t.
<220> FEATURE:
<221> NAME/KEY: misc_feature
<222> LOCATION: (94)..(95)
<223> OTHER INFORMATION: n stands for a, t, g or c.
<220> FEATURE:
<221> NAME/KEY: misc_feature
<222> LOCATION: (97)..(98)
<223> OTHER INFORMATION: n stands for a, t, g or c.
<220> FEATURE:
<221> NAME/KEY: misc_feature
<222> LOCATION: (100)..(101)
<223> OTHER INFORMATION: n stands for a, t, g or c.
<220> FEATURE:
<221> NAME/KEY: misc_feature
<222> LOCATION: (106)..(107)
<223> OTHER INFORMATION: n stands for a, t, g or c.
<220> FEATURE:
<221> NAME/KEY: misc_feature
<222> LOCATION: (109)..(110)
<223> OTHER INFORMATION: n stands for a, t, g or c.
<220> FEATURE:
<221> NAME/KEY: misc_feature
<222> LOCATION: (112)..(113)
<223> OTHER INFORMATION: n stands for a, t, g or c.
<220> FEATURE:
<221> NAME/KEY: misc_feature
<222> LOCATION: (115)..(116)
<223> OTHER INFORMATION: n stands for a, t, g, or c.
<220> FEATURE:
<221> NAME/KEY: misc_feature
<222> LOCATION: (118)..(119)
<223> OTHER INFORMATION: n may be present or absent, and if present n
      stands for a, t, g, or c.
<220> FEATURE:
<221> NAME/KEY: misc_feature
<222> LOCATION: (120)..(120)
<223> OTHER INFORMATION: n may be present or absent, and if present n
      stands for t.
<220> FEATURE:
<221> NAME/KEY: misc_feature
<222> LOCATION: (121)..(122)
<223> OTHER INFORMATION: n may be present or absent, and if present n
      stands for a, t, g, or c.
<220> FEATURE:
<221> NAME/KEY: misc_feature
<222> LOCATION: (123)..(123)
<223> OTHER INFORMATION: n may be present or absent, and if present n
      stands for t.
<220> FEATURE:
<221> NAME/KEY: misc_feature
<222> LOCATION: (124)..(125)
<223> OTHER INFORMATION: n may be present or absent, and if present n
      stands for a, t, g, or c.
<220> FEATURE:
<221> NAME/KEY: misc_feature
<222> LOCATION: (126)..(126)
<223> OTHER INFORMATION: n may be present or absent, and if present n
      stands for t.
<220> FEATURE:
<221> NAME/KEY: misc_feature
<222> LOCATION: (127)..(128)
<223> OTHER INFORMATION: n may be present or absent, and if present n
      stands for a, t, g, or c.
<220> FEATURE:
<221> NAME/KEY: misc_feature
<222> LOCATION: (129)..(129)
<223> OTHER INFORMATION: n may be present or absent, and if present n
      stands for t.
```

```
<220> FEATURE:
<221> NAME/KEY: misc_feature
<222> LOCATION: (130)..(131)
<223> OTHER INFORMATION: n may be present or absent, and if present n
      stands for a, t, g, or c.
<220> FEATURE:
<221> NAME/KEY: misc_feature
<222> LOCATION: (132)..(132)
<223> OTHER INFORMATION: n may be present or absent, and if present n
      stands for t.
<220> FEATURE:
<221> NAME/KEY: misc_feature
<222> LOCATION: (133)..(134)
<223> OTHER INFORMATION: n may be present or absent, and if present n
      stands for a, t, g, or c.
<220> FEATURE:
<221> NAME/KEY: misc_feature
<222> LOCATION: (135)..(135)
<223> OTHER INFORMATION: n may be present or absent, and if present n
      stands for t.
<220> FEATURE:
<221> NAME/KEY: misc_feature
<222> LOCATION: (136)..(137)
<223> OTHER INFORMATION: n may be present or absent, and if present n
      stands for a, t, g, or c.
<220> FEATURE:
<221> NAME/KEY: misc_feature
<222> LOCATION: (138)..(138)
<223> OTHER INFORMATION: n may be present or absent, and if present n
      stands for t.
<220> FEATURE:
<221> NAME/KEY: misc_feature
<222> LOCATION: (139)..(140)
<223> OTHER INFORMATION: n may be present or absent, and if present n
      stands for a, t, g, or c.
<220> FEATURE:
<221> NAME/KEY: misc_feature
<222> LOCATION: (141)..(141)
<223> OTHER INFORMATION: n may be present or absent, and if present n
      stands for t.
<220> FEATURE:
<221> NAME/KEY: misc_feature
<222> LOCATION: (142)..(143)
<223> OTHER INFORMATION: n may be present or absent, and if present n
      stands for a, t, g, or c.
<220> FEATURE:
<221> NAME/KEY: misc_feature
<222> LOCATION: (144)..(144)
<223> OTHER INFORMATION: n may be present or absent, and if present n
      stands for t.
<220> FEATURE:
<221> NAME/KEY: misc_feature
<222> LOCATION: (145)..(146)
<223> OTHER INFORMATION: n may be present or absent, and if present n
      stands for a, t, g, or c.
<220> FEATURE:
<221> NAME/KEY: misc_feature
<222> LOCATION: (147)..(147)
<223> OTHER INFORMATION: n may be present or absent, and if present n
      stands for t.
<220> FEATURE:
<221> NAME/KEY: misc_feature
<222> LOCATION: (148)..(149)
<223> OTHER INFORMATION: n may be present or absent, and if present n
      stands for a, t, g, or c.
<220> FEATURE:
<221> NAME/KEY: misc_feature
<222> LOCATION: (150)..(150)
<223> OTHER INFORMATION: n may be present or absent, and if present n
      stands for t.
<220> FEATURE:
<221> NAME/KEY: misc_feature
<222> LOCATION: (151)..(152)
<223> OTHER INFORMATION: n may be present or absent, and if present n
      stands for a, t, g, or c.
<220> FEATURE:
<221> NAME/KEY: misc_feature
<222> LOCATION: (153)..(153)
<223> OTHER INFORMATION: n may be present or absent, and if present n
``` stands for t.

<400> SEQUENCE: 9
taatacgact cactataggg ttaactttaa gaaggagata tacatatgnn tnntnnnnnn     60
nnnnnnnnnn nnnnnnnnnn nnnnnnnnnn atgnntnntn nttgcnntnn tnntnntnnn    120
nnnnnnnnnn nnnnnnnnnn nnnnnnnnnn nnnggtagcg gcagcggcag ctaggacggg    180
gggcggaaa                                                            189

<210> SEQ ID NO 10
<211> LENGTH: 172
<212> TYPE: RNA
<213> ORGANISM: Artificial Sequence
<220> FEATURE:
<223> OTHER INFORMATION: Nucleic acid sequence of members of NNU mRNA
      Library
<220> FEATURE:
<221> NAME/KEY: misc_feature
<222> LOCATION: (32)..(33)
<223> OTHER INFORMATION: n stands for a, u, g, or c.
<220> FEATURE:
<221> NAME/KEY: misc_feature
<222> LOCATION: (35)..(36)
<223> OTHER INFORMATION: n stands for a, u, g, or c.
<220> FEATURE:
<221> NAME/KEY: misc_feature
<222> LOCATION: (38)..(39)
<223> OTHER INFORMATION: n may be present or absent, and if present n
      stands for a, u, g, or c.
<220> FEATURE:
<221> NAME/KEY: misc_feature
<222> LOCATION: (40)..(40)
<223> OTHER INFORMATION: n may be present or absent, and if present n
      stands for u.
<220> FEATURE:
<221> NAME/KEY: misc_feature
<222> LOCATION: (41)..(42)
<223> OTHER INFORMATION: n may be present or absent, and if present n
      stands for a, u, g, c.
<220> FEATURE:
<221> NAME/KEY: misc_feature
<222> LOCATION: (43)..(43)
<223> OTHER INFORMATION: n may be present or absent, and if present n
      stands for u.
<220> FEATURE:
<221> NAME/KEY: misc_feature
<222> LOCATION: (44)..(45)
<223> OTHER INFORMATION: n may be present or absent, and if present n
      stands for a, u, g, c.
<220> FEATURE:
<221> NAME/KEY: misc_feature
<222> LOCATION: (46)..(46)
<223> OTHER INFORMATION: n may be present or absent, and if present n
      stands for u.
<220> FEATURE:
<221> NAME/KEY: misc_feature
<222> LOCATION: (47)..(48)
<223> OTHER INFORMATION: n may be present or absent, and if present n
      stands for a, u, g, c.
<220> FEATURE:
<221> NAME/KEY: misc_feature
<222> LOCATION: (49)..(49)
<223> OTHER INFORMATION: n may be present or absent, and if present n
      stands for u.
<220> FEATURE:
<221> NAME/KEY: misc_feature
<222> LOCATION: (50)..(51)
<223> OTHER INFORMATION: n may be present or absent, and if present n
      stands for a, u, g, c.
<220> FEATURE:
<221> NAME/KEY: misc_feature
<222> LOCATION: (52)..(52)
<223> OTHER INFORMATION: n may be present or absent, and if present n
      stands for u.
<220> FEATURE:

```
<221> NAME/KEY: misc_feature
<222> LOCATION: (53)..(54)
<223> OTHER INFORMATION: n may be present or absent, and if present n
      stands for a, u, g, c.
<220> FEATURE:
<221> NAME/KEY: misc_feature
<222> LOCATION: (55)..(55)
<223> OTHER INFORMATION: n may be present or absent, and if present n
      stands for u.
<220> FEATURE:
<221> NAME/KEY: misc_feature
<222> LOCATION: (56)..(57)
<223> OTHER INFORMATION: n may be present or absent, and if present n
      stands for a, u, g, c.
<220> FEATURE:
<221> NAME/KEY: misc_feature
<222> LOCATION: (58)..(58)
<223> OTHER INFORMATION: n may be present or absent, and if present n
      stands for u.
<220> FEATURE:
<221> NAME/KEY: misc_feature
<222> LOCATION: (59)..(60)
<223> OTHER INFORMATION: n may be present or absent, and if present n
      stands for a, u, g, c.
<220> FEATURE:
<221> NAME/KEY: misc_feature
<222> LOCATION: (61)..(61)
<223> OTHER INFORMATION: n may be present or absent, and if present n
      stands for u.
<220> FEATURE:
<221> NAME/KEY: misc_feature
<222> LOCATION: (62)..(63)
<223> OTHER INFORMATION: n may be present or absent, and if present n
      stands for a, u, g, c.
<220> FEATURE:
<221> NAME/KEY: misc_feature
<222> LOCATION: (64)..(64)
<223> OTHER INFORMATION: n may be present or absent, and if present n
      stands for u.
<220> FEATURE:
<221> NAME/KEY: misc_feature
<222> LOCATION: (65)..(66)
<223> OTHER INFORMATION: n may be present or absent, and if present n
      stands for a, u, g, c.
<220> FEATURE:
<221> NAME/KEY: misc_feature
<222> LOCATION: (67)..(67)
<223> OTHER INFORMATION: n may be present or absent, and if present n
      stands for u.
<220> FEATURE:
<221> NAME/KEY: misc_feature
<222> LOCATION: (68)..(69)
<223> OTHER INFORMATION: n may be present or absent, and if present n
      stands for a, u, g, c.
<220> FEATURE:
<221> NAME/KEY: misc_feature
<222> LOCATION: (70)..(70)
<223> OTHER INFORMATION: n may be present or absent, and if present n
      stands for u.
<220> FEATURE:
<221> NAME/KEY: misc_feature
<222> LOCATION: (71)..(72)
<223> OTHER INFORMATION: n may be present or absent, and if present n
      stands for a, u, g, c.
<220> FEATURE:
<221> NAME/KEY: misc_feature
<222> LOCATION: (73)..(73)
<223> OTHER INFORMATION: n may be present or absent, and if present n
      stands for u.
<220> FEATURE:
<221> NAME/KEY: misc_feature
<222> LOCATION: (77)..(78)
<223> OTHER INFORMATION: n stands for a, u, g, or c.
<220> FEATURE:
<221> NAME/KEY: misc_feature
<222> LOCATION: (80)..(81)
<223> OTHER INFORMATION: n stands for a, u, g, or c.
<220> FEATURE:
<221> NAME/KEY: misc_feature
```

```
<222> LOCATION: (83)..(84)
<223> OTHER INFORMATION: n stands for a, u, g, or c.
<220> FEATURE:
<221> NAME/KEY: misc_feature
<222> LOCATION: (89)..(90)
<223> OTHER INFORMATION: n stands for a, u, g, or c.
<220> FEATURE:
<221> NAME/KEY: misc_feature
<222> LOCATION: (92)..(93)
<223> OTHER INFORMATION: n stands for a, u, g, or c.
<220> FEATURE:
<221> NAME/KEY: misc_feature
<222> LOCATION: (95)..(96)
<223> OTHER INFORMATION: n stands for a, u, g, or c.
<220> FEATURE:
<221> NAME/KEY: misc_feature
<222> LOCATION: (98)..(99)
<223> OTHER INFORMATION: n stands for a, u, g, or c.
<220> FEATURE:
<221> NAME/KEY: misc_feature
<222> LOCATION: (101)..(102)
<223> OTHER INFORMATION: n may be present or absent, and if present n
      stands for a, u, g, or c.
<220> FEATURE:
<221> NAME/KEY: misc_feature
<222> LOCATION: (103)..(103)
<223> OTHER INFORMATION: n may be present or absent, and if present n
      stands for u.
<220> FEATURE:
<221> NAME/KEY: misc_feature
<222> LOCATION: (104)..(105)
<223> OTHER INFORMATION: n may be present or absent, and if present n
      stands for a, u, g, or c.
<220> FEATURE:
<221> NAME/KEY: misc_feature
<222> LOCATION: (106)..(106)
<223> OTHER INFORMATION: n may be present or absent, and if present n
      stands for u.
<220> FEATURE:
<221> NAME/KEY: misc_feature
<222> LOCATION: (107)..(108)
<223> OTHER INFORMATION: n may be present or absent, and if present n
      stands for a, u, g, or c.
<220> FEATURE:
<221> NAME/KEY: misc_feature
<222> LOCATION: (109)..(109)
<223> OTHER INFORMATION: n may be present or absent, and if present n
      stands for u.
<220> FEATURE:
<221> NAME/KEY: misc_feature
<222> LOCATION: (110)..(111)
<223> OTHER INFORMATION: n may be present or absent, and if present n
      stands for a, u, g, or c.
<220> FEATURE:
<221> NAME/KEY: misc_feature
<222> LOCATION: (112)..(112)
<223> OTHER INFORMATION: n may be present or absent, and if present n
      stands for u.
<220> FEATURE:
<221> NAME/KEY: misc_feature
<222> LOCATION: (113)..(114)
<223> OTHER INFORMATION: n may be present or absent, and if present n
      stands for a, u, g, or c.
<220> FEATURE:
<221> NAME/KEY: misc_feature
<222> LOCATION: (115)..(115)
<223> OTHER INFORMATION: n may be present or absent, and if present n
      stands for u.
<220> FEATURE:
<221> NAME/KEY: misc_feature
<222> LOCATION: (116)..(117)
<223> OTHER INFORMATION: n may be present or absent, and if present n
      stands for a, u, g, or c.
<220> FEATURE:
<221> NAME/KEY: misc_feature
<222> LOCATION: (118)..(118)
<223> OTHER INFORMATION: n may be present or absent, and if present n
      stands for u.
<220> FEATURE:
```

<221> NAME/KEY: misc_feature
<222> LOCATION: (119)..(120)
<223> OTHER INFORMATION: n may be present or absent, and if present n
      stands for a, u, g, or c.
<220> FEATURE:
<221> NAME/KEY: misc_feature
<222> LOCATION: (121)..(121)
<223> OTHER INFORMATION: n may be present or absent, and if present n
      stands for u.
<220> FEATURE:
<221> NAME/KEY: misc_feature
<222> LOCATION: (122)..(123)
<223> OTHER INFORMATION: n may be present or absent, and if present n
      stands for a, u, g, or c.
<220> FEATURE:
<221> NAME/KEY: misc_feature
<222> LOCATION: (124)..(124)
<223> OTHER INFORMATION: n may be present or absent, and if present n
      stands for u.
<220> FEATURE:
<221> NAME/KEY: misc_feature
<222> LOCATION: (125)..(126)
<223> OTHER INFORMATION: n may be present or absent, and if present n
      stands for a, u, g, or c.
<220> FEATURE:
<221> NAME/KEY: misc_feature
<222> LOCATION: (127)..(127)
<223> OTHER INFORMATION: n may be present or absent, and if present n
      stands for u.
<220> FEATURE:
<221> NAME/KEY: misc_feature
<222> LOCATION: (128)..(129)
<223> OTHER INFORMATION: n may be present or absent, and if present n
      stands for a, u, g, or c.
<220> FEATURE:
<221> NAME/KEY: misc_feature
<222> LOCATION: (130)..(130)
<223> OTHER INFORMATION: n may be present or absent, and if present n
      stands for u.
<220> FEATURE:
<221> NAME/KEY: misc_feature
<222> LOCATION: (131)..(132)
<223> OTHER INFORMATION: n may be present or absent, and if present n
      stands for a, u, g, or c.
<220> FEATURE:
<221> NAME/KEY: misc_feature
<222> LOCATION: (133)..(133)
<223> OTHER INFORMATION: n may be present or absent, and if present n
      stands for u.
<220> FEATURE:
<221> NAME/KEY: misc_feature
<222> LOCATION: (134)..(135)
<223> OTHER INFORMATION: n may be present or absent, and if present n
      stands for a, u, g, or c.
<220> FEATURE:
<221> NAME/KEY: misc_feature
<222> LOCATION: (136)..(136)
<223> OTHER INFORMATION: n may be present or absent, and if present n
      stands for u.

<400> SEQUENCE: 10
ggguuaacuu uaagaaggag auauacauau gnnunnunnn nnnnnnnnnn nnnnnnnnnn    60
nnnnnnnnnn nnnaugnnun nunnuugcnn unnunnunnu nnnnnnnnnn nnnnnnnnnn    120
nnnnnnnnnn nnnnnnggua gcggcagcgg cagcuaggac gggggcgga aa             172

<210> SEQ ID NO 11
<211> LENGTH: 16
<212> TYPE: DNA
<213> ORGANISM: Artificial Sequence
<220> FEATURE:
<223> OTHER INFORMATION: Nucleic acid sequence of DNA contained in
      puromycin linker
<220> FEATURE:
<221> NAME/KEY: misc_feature
<223> OTHER INFORMATION: 5'-OH of the DNA is monophosphorylated

<400> SEQUENCE: 11
ctcccgcccc ccgtcc                                                             16

<210> SEQ ID NO 12
<211> LENGTH: 24
<212> TYPE: PRT
<213> ORGANISM: Artificial Sequence
<220> FEATURE:
<223> OTHER INFORMATION: Peptide A-1
<220> FEATURE:
<221> NAME/KEY: misc_feature
<222> LOCATION: (4)..(4)
<223> OTHER INFORMATION: Xaa is (s)-2-amino-6-chlorohex-4-ynoic acid

<400> SEQUENCE: 12

Phe Pro His Xaa Thr Ile Ala Cys Arg Ala Asp Ser Tyr Asp Ser Tyr
1               5                   10                  15

Val Arg Leu Ala Ala Thr Phe Leu
            20

<210> SEQ ID NO 13
<211> LENGTH: 24
<212> TYPE: PRT
<213> ORGANISM: Artificial Sequence
<220> FEATURE:
<223> OTHER INFORMATION: Peptide A-2
<220> FEATURE:
<221> NAME/KEY: misc_feature
<222> LOCATION: (4)..(4)
<223> OTHER INFORMATION: Xaa stands for (s)-2-amino-6-chlorohex-4-ynoic
      acid.
<220> FEATURE:
<221> NAME/KEY: misc_feature
<222> LOCATION: (4)..(4)
<223> OTHER INFORMATION: Xaa is (s)-2-amino-6-chlorohex-4-ynoic acid

<400> SEQUENCE: 13

Phe Pro His Xaa Thr Ile Ala Cys Arg Ala Asp Ser Tyr Asp Ser Tyr
1               5                   10                  15

Val Arg Leu Val Ala Thr Phe Arg
            20

<210> SEQ ID NO 14
<211> LENGTH: 24
<212> TYPE: PRT
<213> ORGANISM: Artificial Sequence
<220> FEATURE:
<223> OTHER INFORMATION: Peptide A-3
<220> FEATURE:
<221> NAME/KEY: misc_feature
<222> LOCATION: (12)..(12)
<223> OTHER INFORMATION: Xaa is (s)-2-amino-6-chlorohex-4-ynoic acid

<400> SEQUENCE: 14

Phe Leu Asn Arg His Asn Asn Ala Tyr Tyr Thr Xaa Gly Tyr Ala Cys
1               5                   10                  15

Leu Gly Arg Leu Tyr Arg Leu Leu
            20

<210> SEQ ID NO 15
<211> LENGTH: 24
<212> TYPE: PRT
<213> ORGANISM: Artificial Sequence
<220> FEATURE:
<223> OTHER INFORMATION: Peptide A-4
<220> FEATURE:
<221> NAME/KEY: misc_feature -continued

```
<222> LOCATION: (12)..(12)
<223> OTHER INFORMATION: Xaa is (s)-2-amino-6-chlorohex-4-ynoic acid

<400> SEQUENCE: 15

Phe Phe Asn Arg His Asn Asn Ala Tyr Tyr Thr Xaa Gly Tyr Ala Cys
1               5                   10                  15
Leu Gly Arg Leu Tyr Arg Leu Leu
            20

<210> SEQ ID NO 16
<211> LENGTH: 20
<212> TYPE: PRT
<213> ORGANISM: Artificial Sequence
<220> FEATURE:
<223> OTHER INFORMATION: Peptide A-5
<220> FEATURE:
<221> NAME/KEY: misc_feature
<222> LOCATION: (4)..(4)
<223> OTHER INFORMATION: Xaa is (s)-2-amino-6-chlorohex-4-ynoic acid

<400> SEQUENCE: 16

Phe Ile Ile Xaa Arg Phe Ser Cys Leu Ala Asp Ser Tyr Asp Ala Ser
1               5                   10                  15
Arg His Ile Phe
            20

<210> SEQ ID NO 17
<211> LENGTH: 24
<212> TYPE: PRT
<213> ORGANISM: Artificial Sequence
<220> FEATURE:
<223> OTHER INFORMATION: Peptide B-1
<220> FEATURE:
<221> NAME/KEY: misc_feature
<222> LOCATION: (16)..(16)
<223> OTHER INFORMATION: Xaa is (s)-2-amino-7-chlorohept-5-ynoic acid

<400> SEQUENCE: 17

Phe Pro Asn Asn Arg Leu Ala Tyr Ala Ala Asp Leu Tyr Asp Ala Xaa
1               5                   10                  15
Arg Ala Leu Cys Asn Pro Thr Ala
            20

<210> SEQ ID NO 18
<211> LENGTH: 24
<212> TYPE: PRT
<213> ORGANISM: Artificial Sequence
<220> FEATURE:
<223> OTHER INFORMATION: Peptide B-4
<220> FEATURE:
<221> NAME/KEY: misc_feature
<222> LOCATION: (4)..(4)
<223> OTHER INFORMATION: Xaa is (s)-2-amino-7-chlorohept-5-ynoic acid

<400> SEQUENCE: 18

Phe Asp Ser Xaa Thr Tyr Arg Cys Tyr Ala Asp Ile Phe Asp Ala His
1               5                   10                  15
Val Arg Leu Val His Ala Leu Asp
            20

<210> SEQ ID NO 19
<211> LENGTH: 24
<212> TYPE: PRT
<213> ORGANISM: Artificial Sequence
<220> FEATURE:
<223> OTHER INFORMATION: Peptide B-5
<220> FEATURE:
```

```
<221> NAME/KEY: misc_feature
<222> LOCATION: (16)..(16)
<223> OTHER INFORMATION: Xaa is (s)-2-amino-7-chlorohept-5-ynoic acid

<400> SEQUENCE: 19

Phe Asp Thr Tyr Arg Tyr Ala Phe Ile Ala Asp Ser His Asp Ala Xaa
1               5                   10                  15

His Thr Ile Cys Asn Thr Arg Tyr
            20

<210> SEQ ID NO 20
<211> LENGTH: 24
<212> TYPE: PRT
<213> ORGANISM: Artificial Sequence
<220> FEATURE:
<223> OTHER INFORMATION: Peptide B-6
<220> FEATURE:
<221> NAME/KEY: misc_feature
<222> LOCATION: (16)..(16)
<223> OTHER INFORMATION: Xaa is (s)-2-amino-7-chlorohept-5-ynoic acid

<400> SEQUENCE: 20

Phe Asp Thr Tyr Arg Tyr Ala Phe Ile Ala Asp Ser His Asp Ala Xaa
1               5                   10                  15

His Thr Ile Cys Asn Thr Arg His
            20

<210> SEQ ID NO 21
<211> LENGTH: 24
<212> TYPE: PRT
<213> ORGANISM: Artificial Sequence
<220> FEATURE:
<223> OTHER INFORMATION: Peptide B-7
<220> FEATURE:
<221> NAME/KEY: misc_feature
<222> LOCATION: (4)..(4)
<223> OTHER INFORMATION: Xaa is (s)-2-amino-7-chlorohept-5-ynoic acid

<400> SEQUENCE: 21

Phe Thr Asp Xaa Leu Ile Tyr Cys Ala Asp Ser Tyr Asp Ala His Ile
1               5                   10                  15

Arg Ile Ala Arg Tyr Leu His Phe
            20

<210> SEQ ID NO 22
<211> LENGTH: 20
<212> TYPE: PRT
<213> ORGANISM: Artificial Sequence
<220> FEATURE:
<223> OTHER INFORMATION: Peptide B-8
<220> FEATURE:
<221> NAME/KEY: misc_feature
<222> LOCATION: (12)..(12)
<223> OTHER INFORMATION: Xaa is (s)-2-amino-7-chlorohept-5-ynoic acid

<400> SEQUENCE: 22

Phe Phe Ala His Arg Ala Asp Leu Tyr Asp Ala Xaa Arg Arg Ile Cys
1               5                   10                  15

Ser Ala Arg Pro
            20

<210> SEQ ID NO 23
<211> LENGTH: 24
<212> TYPE: PRT
<213> ORGANISM: Artificial Sequence
<220> FEATURE:
<223> OTHER INFORMATION: Peptide B-9
```

```
<220> FEATURE:
<221> NAME/KEY: misc_feature
<222> LOCATION: (16)..(16)
<223> OTHER INFORMATION: Xaa is (s)-2-amino-7-chlorohept-5-ynoic acid

<400> SEQUENCE: 23

Phe Arg Arg Phe Ala Tyr Arg Ser Asp Leu His Asp Ala Tyr Ile Xaa
1               5                   10                  15

Phe Arg Arg Cys Ile Asn Arg His
            20

<210> SEQ ID NO 24
<211> LENGTH: 24
<212> TYPE: PRT
<213> ORGANISM: Artificial Sequence
<220> FEATURE:
<223> OTHER INFORMATION: Peptide C-1
<220> FEATURE:
<221> NAME/KEY: misc_feature
<222> LOCATION: (4)..(4)
<223> OTHER INFORMATION: Xaa is (s)-2-amino-8-chlorooct-6-ynoic acid

<400> SEQUENCE: 24

Phe Thr Phe Xaa Pro Leu Ile Cys Arg Ala Asp Asp Phe Asp Ala Ile
1               5                   10                  15

Arg Ile Leu Arg Gly Ile Val Asn
            20

<210> SEQ ID NO 25
<211> LENGTH: 24
<212> TYPE: PRT
<213> ORGANISM: Artificial Sequence
<220> FEATURE:
<223> OTHER INFORMATION: Peptide C-2
<220> FEATURE:
<221> NAME/KEY: misc_feature
<222> LOCATION: (16)..(16)
<223> OTHER INFORMATION: Xaa is (s)-2-amino-8-chlorooct-6-ynoic acid

<400> SEQUENCE: 25

Phe Asp His Asn Arg Tyr Arg Ala Leu Ala Asp Ile Asp Asn Ala Xaa
1               5                   10                  15

Arg Ile Leu Cys Ala Arg Val Leu
            20

<210> SEQ ID NO 26
<211> LENGTH: 24
<212> TYPE: PRT
<213> ORGANISM: Artificial Sequence
<220> FEATURE:
<223> OTHER INFORMATION: Control peptide A-1A

<400> SEQUENCE: 26

Phe Pro His Ala Thr Ile Ala Ala Arg Ala Asp Ser Tyr Asp Ser Tyr
1               5                   10                  15

Val Arg Leu Ala Ala Thr Phe Leu
            20

<210> SEQ ID NO 27
<211> LENGTH: 24
<212> TYPE: PRT
<213> ORGANISM: Artificial Sequence
<220> FEATURE:
<223> OTHER INFORMATION: Control peptide A-2A

<400> SEQUENCE: 27
```

Phe Pro His Ala Thr Ile Ala Ala Arg Ala Asp Ser Tyr Asp Ser Tyr
1               5                   10                  15

Val Arg Leu Val Ala Thr Phe Arg
            20

<210> SEQ ID NO 28
<211> LENGTH: 24
<212> TYPE: PRT
<213> ORGANISM: Artificial Sequence
<220> FEATURE:
<223> OTHER INFORMATION: Control peptide A-3A

<400> SEQUENCE: 28

Phe Leu Asn Arg His Asn Asn Ala Tyr Tyr Thr Ala Gly Tyr Ala Ala
1               5                   10                  15

Leu Gly Arg Leu Tyr Arg Leu Leu
            20

<210> SEQ ID NO 29
<211> LENGTH: 24
<212> TYPE: PRT
<213> ORGANISM: Artificial Sequence
<220> FEATURE:
<223> OTHER INFORMATION: Control peptide A-4A

<400> SEQUENCE: 29

Phe Phe Asn Arg His Asn Asn Ala Tyr Tyr Thr Ala Gly Tyr Ala Ala
1               5                   10                  15

Leu Gly Arg Leu Tyr Arg Leu Leu
            20

<210> SEQ ID NO 30
<211> LENGTH: 20
<212> TYPE: PRT
<213> ORGANISM: Artificial Sequence
<220> FEATURE:
<223> OTHER INFORMATION: Control peptide A-5A

<400> SEQUENCE: 30

Phe Ile Ile Ala Arg Phe Ser Ala Leu Ala Asp Ser Tyr Asp Ala Ser
1               5                   10                  15

Arg His Ile Phe
            20

<210> SEQ ID NO 31
<211> LENGTH: 69
<212> TYPE: RNA
<213> ORGANISM: Artificial Sequence
<220> FEATURE:
<223> OTHER INFORMATION: Nucleic acid sequence of coding region of
      peptides in each pool of mRNA library
<220> FEATURE:
<221> NAME/KEY: misc_feature
<222> LOCATION: (4)..(5)
<223> OTHER INFORMATION: n stands for a, u, g or c.
<220> FEATURE:
<221> NAME/KEY: misc_feature
<222> LOCATION: (7)..(8)
<223> OTHER INFORMATION: n stands for a, u, g or c.
<220> FEATURE:
<221> NAME/KEY: misc_feature
<222> LOCATION: (13)..(14)
<223> OTHER INFORMATION: n stands for a, u, g or c.
<220> FEATURE:
<221> NAME/KEY: misc_feature
<222> LOCATION: (16)..(17)
<223> OTHER INFORMATION: n stands for a, u, g or c.
<220> FEATURE:

```
<221> NAME/KEY: misc_feature
<222> LOCATION: (19)..(20)
<223> OTHER INFORMATION: n stands for a, u, g or c.
<220> FEATURE:
<221> NAME/KEY: misc_feature
<222> LOCATION: (25)..(26)
<223> OTHER INFORMATION: n stands for a, u, g or c.
<220> FEATURE:
<221> NAME/KEY: misc_feature
<222> LOCATION: (28)..(29)
<223> OTHER INFORMATION: n stands for a, u, g or c.
<220> FEATURE:
<221> NAME/KEY: misc_feature
<222> LOCATION: (31)..(32)
<223> OTHER INFORMATION: n stands for a, u, g or c.
<220> FEATURE:
<221> NAME/KEY: misc_feature
<222> LOCATION: (34)..(35)
<223> OTHER INFORMATION: n stands for a, u, g or c.
<220> FEATURE:
<221> NAME/KEY: misc_feature
<222> LOCATION: (37)..(38)
<223> OTHER INFORMATION: n stands for a, u, g or c.
<220> FEATURE:
<221> NAME/KEY: misc_feature
<222> LOCATION: (40)..(41)
<223> OTHER INFORMATION: n stands for a, u, g or c.
<220> FEATURE:
<221> NAME/KEY: misc_feature
<222> LOCATION: (43)..(44)
<223> OTHER INFORMATION: n stands for a, u, g or c.
<220> FEATURE:
<221> NAME/KEY: misc_feature
<222> LOCATION: (46)..(47)
<223> OTHER INFORMATION: n stands for a, u, g or c.

<400> SEQUENCE: 31
augnnunnua ugnnunnunn uugcnnunnu nnunnunnun nunnunnugg uagcggcagc      60
ggcagcuag                                                             69

<210> SEQ ID NO 32
<211> LENGTH: 69
<212> TYPE: RNA
<213> ORGANISM: Artificial Sequence
<220> FEATURE:
<223> OTHER INFORMATION: Nucleic acid sequence of coding region of
      peptides in each pool of mRNA library
<220> FEATURE:
<221> NAME/KEY: misc_feature
<222> LOCATION: (4)..(5)
<223> OTHER INFORMATION: n stands for a, u, g or c.
<220> FEATURE:
<221> NAME/KEY: misc_feature
<222> LOCATION: (7)..(8)
<223> OTHER INFORMATION: n stands for a, u, g or c.
<220> FEATURE:
<221> NAME/KEY: misc_feature
<222> LOCATION: (10)..(11)
<223> OTHER INFORMATION: n stands for a, u, g or c.
<220> FEATURE:
<221> NAME/KEY: misc_feature
<222> LOCATION: (13)..(14)
<223> OTHER INFORMATION: n stands for a, u, g or c.
<220> FEATURE:
<221> NAME/KEY: misc_feature
<222> LOCATION: (16)..(17)
<223> OTHER INFORMATION: n stands for a, u, g or c.
<220> FEATURE:
<221> NAME/KEY: misc_feature
<222> LOCATION: (19)..(20)
<223> OTHER INFORMATION: n stands for a, u, g or c.
<220> FEATURE:
<221> NAME/KEY: misc_feature
<222> LOCATION: (25)..(26)
<223> OTHER INFORMATION: n stands for a, u, g or c.
<220> FEATURE:
```

<221> NAME/KEY: misc_feature
<222> LOCATION: (28)..(29)
<223> OTHER INFORMATION: n stands for a, u, g or c.
<220> FEATURE:
<221> NAME/KEY: misc_feature
<222> LOCATION: (31)..(32)
<223> OTHER INFORMATION: n stands for a, u, g or c.
<220> FEATURE:
<221> NAME/KEY: misc_feature
<222> LOCATION: (37)..(38)
<223> OTHER INFORMATION: n stands for a, u, g or c.
<220> FEATURE:
<221> NAME/KEY: misc_feature
<222> LOCATION: (40)..(41)
<223> OTHER INFORMATION: n stands for a, u, g or c.
<220> FEATURE:
<221> NAME/KEY: misc_feature
<222> LOCATION: (43)..(44)
<223> OTHER INFORMATION: n stands for a, u, g or c.
<220> FEATURE:
<221> NAME/KEY: misc_feature
<222> LOCATION: (46)..(47)
<223> OTHER INFORMATION: n stands for a, u, g or c.

<400> SEQUENCE: 32
augnnunnun nunnunnunn uaugnnunnu nnuugcnnun nunnunnugg uagcggcagc    60
ggcagcuag                                                            69

<210> SEQ ID NO 33
<211> LENGTH: 78
<212> TYPE: RNA
<213> ORGANISM: Artificial Sequence
<220> FEATURE:
<223> OTHER INFORMATION: Nucleic acid sequence of coding region of
      peptides in each pool of mRNA library
<220> FEATURE:
<221> NAME/KEY: misc_feature
<222> LOCATION: (4)..(5)
<223> OTHER INFORMATION: n stands for a, u, g or c.
<220> FEATURE:
<221> NAME/KEY: misc_feature
<222> LOCATION: (7)..(8)
<223> OTHER INFORMATION: n stands for a, u, g or c.
<220> FEATURE:
<221> NAME/KEY: misc_feature
<222> LOCATION: (13)..(14)
<223> OTHER INFORMATION: n stands for a, u, g or c.
<220> FEATURE:
<221> NAME/KEY: misc_feature
<222> LOCATION: (16)..(17)
<223> OTHER INFORMATION: n stands for a, u, g or c.
<220> FEATURE:
<221> NAME/KEY: misc_feature
<222> LOCATION: (19)..(20)
<223> OTHER INFORMATION: n stands for a, u, g or c.
<220> FEATURE:
<221> NAME/KEY: misc_feature
<222> LOCATION: (25)..(26)
<223> OTHER INFORMATION: n stands for a, u, g or c.
<220> FEATURE:
<221> NAME/KEY: misc_feature
<222> LOCATION: (28)..(29)
<223> OTHER INFORMATION: n stands for a, u, g or c.
<220> FEATURE:
<221> NAME/KEY: misc_feature
<222> LOCATION: (31)..(32)
<223> OTHER INFORMATION: n stands for a, u, g or c.
<220> FEATURE:
<221> NAME/KEY: misc_feature
<222> LOCATION: (34)..(35)
<223> OTHER INFORMATION: n stands for a, u, g or c.
<220> FEATURE:
<221> NAME/KEY: misc_feature
<222> LOCATION: (37)..(38)
<223> OTHER INFORMATION: n stands for a, u, g or c.
<220> FEATURE:

```
<221> NAME/KEY: misc_feature
<222> LOCATION: (40)..(41)
<223> OTHER INFORMATION: n stands for a, u, g or c.
<220> FEATURE:
<221> NAME/KEY: misc_feature
<222> LOCATION: (43)..(44)
<223> OTHER INFORMATION: n stands for a, u, g or c.
<220> FEATURE:
<221> NAME/KEY: misc_feature
<222> LOCATION: (46)..(47)
<223> OTHER INFORMATION: n stands for a, u, g or c.
<220> FEATURE:
<221> NAME/KEY: misc_feature
<222> LOCATION: (49)..(50)
<223> OTHER INFORMATION: n stands for a, u, g or c.
<220> FEATURE:
<221> NAME/KEY: misc_feature
<222> LOCATION: (52)..(53)
<223> OTHER INFORMATION: n stands for a, u, g or c.
<220> FEATURE:
<221> NAME/KEY: misc_feature
<222> LOCATION: (55)..(56)
<223> OTHER INFORMATION: n stands for a, u, g or c.

<400> SEQUENCE: 33
augnnunnua ugnnunnunn uugcnnunnu nnunnunnun nunnunnunn unnunnuggu    60
agcggcagcg gcagcuag                                                 78

<210> SEQ ID NO 34
<211> LENGTH: 81
<212> TYPE: RNA
<213> ORGANISM: Artificial Sequence
<220> FEATURE:
<223> OTHER INFORMATION: Nucleic acid sequence of coding region of
      peptides in each pool of mRNA library
<220> FEATURE:
<221> NAME/KEY: misc_feature
<222> LOCATION: (4)..(5)
<223> OTHER INFORMATION: n stands for a, u, g or c.
<220> FEATURE:
<221> NAME/KEY: misc_feature
<222> LOCATION: (7)..(8)
<223> OTHER INFORMATION: n stands for a, u, g or c.
<220> FEATURE:
<221> NAME/KEY: misc_feature
<222> LOCATION: (10)..(11)
<223> OTHER INFORMATION: n stands for a, u, g or c.
<220> FEATURE:
<221> NAME/KEY: misc_feature
<222> LOCATION: (13)..(14)
<223> OTHER INFORMATION: n stands for a, u, g or c.
<220> FEATURE:
<221> NAME/KEY: misc_feature
<222> LOCATION: (16)..(17)
<223> OTHER INFORMATION: n stands for a, u, g or c.
<220> FEATURE:
<221> NAME/KEY: misc_feature
<222> LOCATION: (19)..(20)
<223> OTHER INFORMATION: n stands for a, u, g or c.
<220> FEATURE:
<221> NAME/KEY: misc_feature
<222> LOCATION: (25)..(26)
<223> OTHER INFORMATION: n stands for a, u, g or c.
<220> FEATURE:
<221> NAME/KEY: misc_feature
<222> LOCATION: (28)..(29)
<223> OTHER INFORMATION: n stands for a, u, g or c.
<220> FEATURE:
<221> NAME/KEY: misc_feature
<222> LOCATION: (31)..(32)
<223> OTHER INFORMATION: n stands for a, u, g or c.
<220> FEATURE:
<221> NAME/KEY: misc_feature
<222> LOCATION: (37)..(38)
<223> OTHER INFORMATION: n stands for a, u, g or c.
<220> FEATURE:
```

```
<221> NAME/KEY: misc_feature
<222> LOCATION: (40)..(41)
<223> OTHER INFORMATION: n stands for a, u, g or c.
<220> FEATURE:
<221> NAME/KEY: misc_feature
<222> LOCATION: (43)..(44)
<223> OTHER INFORMATION: n stands for a, u, g or c.
<220> FEATURE:
<221> NAME/KEY: misc_feature
<222> LOCATION: (46)..(47)
<223> OTHER INFORMATION: n stands for a, u, g or c.
<220> FEATURE:
<221> NAME/KEY: misc_feature
<222> LOCATION: (49)..(50)
<223> OTHER INFORMATION: n stands for a, u, g or c.
<220> FEATURE:
<221> NAME/KEY: misc_feature
<222> LOCATION: (52)..(53)
<223> OTHER INFORMATION: n stands for a, u, g or c.
<220> FEATURE:
<221> NAME/KEY: misc_feature
<222> LOCATION: (55)..(56)
<223> OTHER INFORMATION: n stands for a, u, g or c.
<220> FEATURE:
<221> NAME/KEY: misc_feature
<222> LOCATION: (58)..(59)
<223> OTHER INFORMATION: n stands for a, u, g or c.

<400> SEQUENCE: 34
augnnunnun nunnunnunn uaugnnunnu nnuugcnnun nunnunnunn unnunnunnu    60
gguagcggca gcggcagcua g                                              81

<210> SEQ ID NO 35
<211> LENGTH: 81
<212> TYPE: RNA
<213> ORGANISM: Artificial Sequence
<220> FEATURE:
<223> OTHER INFORMATION: Nucleic acid sequence of coding region of
      peptides in each pool of mRNA library
<220> FEATURE:
<221> NAME/KEY: misc_feature
<222> LOCATION: (4)..(5)
<223> OTHER INFORMATION: n stands for a, u, g or c.
<220> FEATURE:
<221> NAME/KEY: misc_feature
<222> LOCATION: (7)..(8)
<223> OTHER INFORMATION: n stands for a, u, g or c.
<220> FEATURE:
<221> NAME/KEY: misc_feature
<222> LOCATION: (10)..(11)
<223> OTHER INFORMATION: n stands for a, u, g or c.
<220> FEATURE:
<221> NAME/KEY: misc_feature
<222> LOCATION: (13)..(14)
<223> OTHER INFORMATION: n stands for a, u, g or c.
<220> FEATURE:
<221> NAME/KEY: misc_feature
<222> LOCATION: (16)..(17)
<223> OTHER INFORMATION: n stands for a, u, g or c.
<220> FEATURE:
<221> NAME/KEY: misc_feature
<222> LOCATION: (19)..(20)
<223> OTHER INFORMATION: n stands for a, u, g or c.
<220> FEATURE:
<221> NAME/KEY: misc_feature
<222> LOCATION: (22)..(23)
<223> OTHER INFORMATION: n stands for a, u, g or c.
<220> FEATURE:
<221> NAME/KEY: misc_feature
<222> LOCATION: (25)..(26)
<223> OTHER INFORMATION: n stands for a, u, g or c.
<220> FEATURE:
<221> NAME/KEY: misc_feature
<222> LOCATION: (28)..(29)
<223> OTHER INFORMATION: n stands for a, u, g or c.
<220> FEATURE:
```

```
<221> NAME/KEY: misc_feature
<222> LOCATION: (31)..(32)
<223> OTHER INFORMATION: n stands for a, u, g or c.
<220> FEATURE:
<221> NAME/KEY: misc_feature
<222> LOCATION: (37)..(38)
<223> OTHER INFORMATION: n stands for a, u, g or c.
<220> FEATURE:
<221> NAME/KEY: misc_feature
<222> LOCATION: (40)..(41)
<223> OTHER INFORMATION: n stands for a, u, g or c.
<220> FEATURE:
<221> NAME/KEY: misc_feature
<222> LOCATION: (43)..(44)
<223> OTHER INFORMATION: n stands for a, u, g or c.
<220> FEATURE:
<221> NAME/KEY: misc_feature
<222> LOCATION: (49)..(50)
<223> OTHER INFORMATION: n stands for a, u, g or c.
<220> FEATURE:
<221> NAME/KEY: misc_feature
<222> LOCATION: (52)..(53)
<223> OTHER INFORMATION: n stands for a, u, g or c.
<220> FEATURE:
<221> NAME/KEY: misc_feature
<222> LOCATION: (55)..(56)
<223> OTHER INFORMATION: n stands for a, u, g or c.
<220> FEATURE:
<221> NAME/KEY: misc_feature
<222> LOCATION: (58)..(59)
<223> OTHER INFORMATION: n stands for a, u, g or c.

<400> SEQUENCE: 35
augnnunnun nunnunnunn unnunnunnu nnuaugnnun nunnuugcnn unnunnunnu        60
gguagcggca gcggcagcua g                                                 81

<210> SEQ ID NO 36
<211> LENGTH: 93
<212> TYPE: RNA
<213> ORGANISM: Artificial Sequence
<220> FEATURE:
<223> OTHER INFORMATION: Nucleic acid sequence of coding region of
      peptides in each pool of mRNA library
<220> FEATURE:
<221> NAME/KEY: misc_feature
<222> LOCATION: (4)..(5)
<223> OTHER INFORMATION: n stands for a, u, g or c.
<220> FEATURE:
<221> NAME/KEY: misc_feature
<222> LOCATION: (7)..(8)
<223> OTHER INFORMATION: n stands for a, u, g or c.
<220> FEATURE:
<221> NAME/KEY: misc_feature
<222> LOCATION: (13)..(14)
<223> OTHER INFORMATION: n stands for a, u, g or c.
<220> FEATURE:
<221> NAME/KEY: misc_feature
<222> LOCATION: (16)..(17)
<223> OTHER INFORMATION: n stands for a, u, g or c.
<220> FEATURE:
<221> NAME/KEY: misc_feature
<222> LOCATION: (19)..(20)
<223> OTHER INFORMATION: n stands for a, u, g or c.
<220> FEATURE:
<221> NAME/KEY: misc_feature
<222> LOCATION: (25)..(26)
<223> OTHER INFORMATION: n stands for a, u, g or c.
<220> FEATURE:
<221> NAME/KEY: misc_feature
<222> LOCATION: (28)..(29)
<223> OTHER INFORMATION: n stands for a, u, g or c.
<220> FEATURE:
<221> NAME/KEY: misc_feature
<222> LOCATION: (31)..(32)
<223> OTHER INFORMATION: n stands for a, u, g or c.
<220> FEATURE:
```

```
<221> NAME/KEY: misc_feature
<222> LOCATION: (34)..(35)
<223> OTHER INFORMATION: n stands for a, u, g or c.
<220> FEATURE:
<221> NAME/KEY: misc_feature
<222> LOCATION: (37)..(38)
<223> OTHER INFORMATION: n stands for a, u, g or c.
<220> FEATURE:
<221> NAME/KEY: misc_feature
<222> LOCATION: (40)..(41)
<223> OTHER INFORMATION: n stands for a, u, g or c.
<220> FEATURE:
<221> NAME/KEY: misc_feature
<222> LOCATION: (43)..(44)
<223> OTHER INFORMATION: n stands for a, u, g or c.
<220> FEATURE:
<221> NAME/KEY: misc_feature
<222> LOCATION: (46)..(47)
<223> OTHER INFORMATION: n stands for a, u, g or c.
<220> FEATURE:
<221> NAME/KEY: misc_feature
<222> LOCATION: (49)..(50)
<223> OTHER INFORMATION: n stands for a, u, g or c.
<220> FEATURE:
<221> NAME/KEY: misc_feature
<222> LOCATION: (52)..(53)
<223> OTHER INFORMATION: n stands for a, u, g or c.
<220> FEATURE:
<221> NAME/KEY: misc_feature
<222> LOCATION: (55)..(56)
<223> OTHER INFORMATION: n stands for a, u, g or c.
<220> FEATURE:
<221> NAME/KEY: misc_feature
<222> LOCATION: (58)..(59)
<223> OTHER INFORMATION: n stands for a, u, g or c.
<220> FEATURE:
<221> NAME/KEY: misc_feature
<222> LOCATION: (61)..(62)
<223> OTHER INFORMATION: n stands for a, u, g or c.
<220> FEATURE:
<221> NAME/KEY: misc_feature
<222> LOCATION: (64)..(65)
<223> OTHER INFORMATION: n stands for a, u, g or c.
<220> FEATURE:
<221> NAME/KEY: misc_feature
<222> LOCATION: (67)..(68)
<223> OTHER INFORMATION: n stands for a, u, g or c.
<220> FEATURE:
<221> NAME/KEY: misc_feature
<222> LOCATION: (70)..(71)
<223> OTHER INFORMATION: n stands for a, u, g or c.

<400> SEQUENCE: 36
augnnunnua ugnnunnunn uugcnnunnu nnunnunnun nunnunnunn unnunnunnu      60
nnunnunnun nugguagcgg cagcggcagc uag                                  93

<210> SEQ ID NO 37
<211> LENGTH: 93
<212> TYPE: RNA
<213> ORGANISM: Artificial Sequence
<220> FEATURE:
<223> OTHER INFORMATION: Nucleic acid sequence of coding region of
      peptides in each pool of mRNA library
<220> FEATURE:
<221> NAME/KEY: misc_feature
<222> LOCATION: (4)..(5)
<223> OTHER INFORMATION: n stands for a, u, g or c.
<220> FEATURE:
<221> NAME/KEY: misc_feature
<222> LOCATION: (7)..(8)
<223> OTHER INFORMATION: n stands for a, u, g or c.
<220> FEATURE:
<221> NAME/KEY: misc_feature
<222> LOCATION: (10)..(11)
<223> OTHER INFORMATION: n stands for a, u, g or c.
<220> FEATURE:
```

```
<221> NAME/KEY: misc_feature
<222> LOCATION: (13)..(14)
<223> OTHER INFORMATION: n stands for a, u, g or c.
<220> FEATURE:
<221> NAME/KEY: misc_feature
<222> LOCATION: (16)..(17)
<223> OTHER INFORMATION: n stands for a, u, g or c.
<220> FEATURE:
<221> NAME/KEY: misc_feature
<222> LOCATION: (19)..(20)
<223> OTHER INFORMATION: n stands for a, u, g or c.
<220> FEATURE:
<221> NAME/KEY: misc_feature
<222> LOCATION: (25)..(26)
<223> OTHER INFORMATION: n stands for a, u, g or c.
<220> FEATURE:
<221> NAME/KEY: misc_feature
<222> LOCATION: (28)..(29)
<223> OTHER INFORMATION: n stands for a, u, g or c.
<220> FEATURE:
<221> NAME/KEY: misc_feature
<222> LOCATION: (31)..(32)
<223> OTHER INFORMATION: n stands for a, u, g or c.
<220> FEATURE:
<221> NAME/KEY: misc_feature
<222> LOCATION: (37)..(38)
<223> OTHER INFORMATION: n stands for a, u, g or c.
<220> FEATURE:
<221> NAME/KEY: misc_feature
<222> LOCATION: (40)..(41)
<223> OTHER INFORMATION: n stands for a, u, g or c.
<220> FEATURE:
<221> NAME/KEY: misc_feature
<222> LOCATION: (43)..(44)
<223> OTHER INFORMATION: n stands for a, u, g or c.
<220> FEATURE:
<221> NAME/KEY: misc_feature
<222> LOCATION: (46)..(47)
<223> OTHER INFORMATION: n stands for a, u, g or c.
<220> FEATURE:
<221> NAME/KEY: misc_feature
<222> LOCATION: (49)..(50)
<223> OTHER INFORMATION: n stands for a, u, g or c.
<220> FEATURE:
<221> NAME/KEY: misc_feature
<222> LOCATION: (52)..(53)
<223> OTHER INFORMATION: n stands for a, u, g or c.
<220> FEATURE:
<221> NAME/KEY: misc_feature
<222> LOCATION: (55)..(58)
<223> OTHER INFORMATION: n stands for a, u, g or c.
<220> FEATURE:
<221> NAME/KEY: misc_feature
<222> LOCATION: (58)..(59)
<223> OTHER INFORMATION: n stands for a, u, g or c.
<220> FEATURE:
<221> NAME/KEY: misc_feature
<222> LOCATION: (61)..(62)
<223> OTHER INFORMATION: n stands for a, u, g or c.
<220> FEATURE:
<221> NAME/KEY: misc_feature
<222> LOCATION: (64)..(65)
<223> OTHER INFORMATION: n stands for a, u, g or c.
<220> FEATURE:
<221> NAME/KEY: misc_feature
<222> LOCATION: (67)..(68)
<223> OTHER INFORMATION: n stands for a, u, g or c.
<220> FEATURE:
<221> NAME/KEY: misc_feature
<222> LOCATION: (70)..(71)
<223> OTHER INFORMATION: n stands for a, u, g or c.

<400> SEQUENCE: 37
augnnunnun nunnunnunn uaugnnunnu nnuugcnnun nunnunnunn unnunnunnu    60
nnunnunnun nugguagcgg cagcggcagc uag                                 93
```

```
<210> SEQ ID NO 38
<211> LENGTH: 93
<212> TYPE: RNA
<213> ORGANISM: Artificial Sequence
<220> FEATURE:
<223> OTHER INFORMATION: Nucleic acid sequence of coding region of
      peptides in each pool of mRNA library
<220> FEATURE:
<221> NAME/KEY: misc_feature
<222> LOCATION: (4)..(5)
<223> OTHER INFORMATION: n stands for a, u, g or c.
<220> FEATURE:
<221> NAME/KEY: misc_feature
<222> LOCATION: (7)..(8)
<223> OTHER INFORMATION: n stands for a, u, g or c.
<220> FEATURE:
<221> NAME/KEY: misc_feature
<222> LOCATION: (10)..(11)
<223> OTHER INFORMATION: n stands for a, u, g or c.
<220> FEATURE:
<221> NAME/KEY: misc_feature
<222> LOCATION: (13)..(14)
<223> OTHER INFORMATION: n stands for a, u, g or c.
<220> FEATURE:
<221> NAME/KEY: misc_feature
<222> LOCATION: (16)..(17)
<223> OTHER INFORMATION: n stands for a, u, g or c.
<220> FEATURE:
<221> NAME/KEY: misc_feature
<222> LOCATION: (19)..(20)
<223> OTHER INFORMATION: n stands for a, u, g or c.
<220> FEATURE:
<221> NAME/KEY: misc_feature
<222> LOCATION: (22)..(23)
<223> OTHER INFORMATION: n stands for a, u, g or c.
<220> FEATURE:
<221> NAME/KEY: misc_feature
<222> LOCATION: (25)..(26)
<223> OTHER INFORMATION: n stands for a, u, g or c.
<220> FEATURE:
<221> NAME/KEY: misc_feature
<222> LOCATION: (28)..(29)
<223> OTHER INFORMATION: n stands for a, u, g or c.
<220> FEATURE:
<221> NAME/KEY: misc_feature
<222> LOCATION: (31)..(32)
<223> OTHER INFORMATION: n stands for a, u, g or c.
<220> FEATURE:
<221> NAME/KEY: misc_feature
<222> LOCATION: (37)..(38)
<223> OTHER INFORMATION: n stands for a, u, g or c.
<220> FEATURE:
<221> NAME/KEY: misc_feature
<222> LOCATION: (40)..(41)
<223> OTHER INFORMATION: n stands for a, u, g or c.
<220> FEATURE:
<221> NAME/KEY: misc_feature
<222> LOCATION: (43)..(44)
<223> OTHER INFORMATION: n stands for a, u, g or c.
<220> FEATURE:
<221> NAME/KEY: misc_feature
<222> LOCATION: (49)..(50)
<223> OTHER INFORMATION: n stands for a, u, g or c.
<220> FEATURE:
<221> NAME/KEY: misc_feature
<222> LOCATION: (52)..(53)
<223> OTHER INFORMATION: n stands for a, u, g or c.
<220> FEATURE:
<221> NAME/KEY: misc_feature
<222> LOCATION: (55)..(56)
<223> OTHER INFORMATION: n stands for a, u, g or c.
<220> FEATURE:
<221> NAME/KEY: misc_feature
<222> LOCATION: (58)..(59)
<223> OTHER INFORMATION: n stands for a, u, g or c.
<220> FEATURE:
<221> NAME/KEY: misc_feature
<222> LOCATION: (61)..(62)
<223> OTHER INFORMATION: n stands for a, u, g or c.
```

```
<220> FEATURE:
<221> NAME/KEY: misc_feature
<222> LOCATION: (64)..(65)
<223> OTHER INFORMATION: n stands for a, u, g or c.
<220> FEATURE:
<221> NAME/KEY: misc_feature
<222> LOCATION: (67)..(68)
<223> OTHER INFORMATION: n stands for a, u, g or c.
<220> FEATURE:
<221> NAME/KEY: misc_feature
<222> LOCATION: (70)..(71)
<223> OTHER INFORMATION: n stands for a, u, g or c.

<400> SEQUENCE: 38
augnnunnun nunnunnunn unnunnunnu nnuaugnnun nunnuugcnn unnunnunnu    60
nnunnunnun nugguagcgg cagcggcagc uag                                 93

<210> SEQ ID NO 39
<211> LENGTH: 93
<212> TYPE: RNA
<213> ORGANISM: Artificial Sequence
<220> FEATURE:
<223> OTHER INFORMATION: Nucleic acid sequence of coding region of
      peptides in each pool of mRNA library
<220> FEATURE:
<221> NAME/KEY: misc_feature
<222> LOCATION: (4)..(5)
<223> OTHER INFORMATION: n stands for a, u, g or c.
<220> FEATURE:
<221> NAME/KEY: misc_feature
<222> LOCATION: (7)..(8)
<223> OTHER INFORMATION: n stands for a, u, g or c.
<220> FEATURE:
<221> NAME/KEY: misc_feature
<222> LOCATION: (10)..(11)
<223> OTHER INFORMATION: n stands for a, u, g or c.
<220> FEATURE:
<221> NAME/KEY: misc_feature
<222> LOCATION: (13)..(14)
<223> OTHER INFORMATION: n stands for a, u, g or c.
<220> FEATURE:
<221> NAME/KEY: misc_feature
<222> LOCATION: (16)..(17)
<223> OTHER INFORMATION: n stands for a, u, g or c.
<220> FEATURE:
<221> NAME/KEY: misc_feature
<222> LOCATION: (19)..(20)
<223> OTHER INFORMATION: n stands for a, u, g or c.
<220> FEATURE:
<221> NAME/KEY: misc_feature
<222> LOCATION: (22)..(23)
<223> OTHER INFORMATION: n stands for a, u, g or c.
<220> FEATURE:
<221> NAME/KEY: misc_feature
<222> LOCATION: (25)..(26)
<223> OTHER INFORMATION: n stands for a, u, g or c.
<220> FEATURE:
<221> NAME/KEY: misc_feature
<222> LOCATION: (28)..(29)
<223> OTHER INFORMATION: n stands for a, u, g or c.
<220> FEATURE:
<221> NAME/KEY: misc_feature
<222> LOCATION: (31)..(32)
<223> OTHER INFORMATION: n stands for a, u, g or c.
<220> FEATURE:
<221> NAME/KEY: misc_feature
<222> LOCATION: (34)..(35)
<223> OTHER INFORMATION: n stands for a, u, g or c.
<220> FEATURE:
<221> NAME/KEY: misc_feature
<222> LOCATION: (37)..(38)
<223> OTHER INFORMATION: n stands for a, u, g or c.
<220> FEATURE:
<221> NAME/KEY: misc_feature
<222> LOCATION: (40)..(41)
<223> OTHER INFORMATION: n stands for a, u, g or c.
```

```
<220> FEATURE:
<221> NAME/KEY: misc_feature
<222> LOCATION: (43)..(44)
<223> OTHER INFORMATION: n stands for a, u, g or c.
<220> FEATURE:
<221> NAME/KEY: misc_feature
<222> LOCATION: (49)..(50)
<223> OTHER INFORMATION: n stands for a, u, g or c.
<220> FEATURE:
<221> NAME/KEY: misc_feature
<222> LOCATION: (52)..(53)
<223> OTHER INFORMATION: n stands for a, u, g or c.
<220> FEATURE:
<221> NAME/KEY: misc_feature
<222> LOCATION: (55)..(56)
<223> OTHER INFORMATION: n stands for a, u, g or c.
<220> FEATURE:
<221> NAME/KEY: misc_feature
<222> LOCATION: (61)..(62)
<223> OTHER INFORMATION: n stands for a, u, g or c.
<220> FEATURE:
<221> NAME/KEY: misc_feature
<222> LOCATION: (64)..(65)
<223> OTHER INFORMATION: n stands for a, u, g or c.
<220> FEATURE:
<221> NAME/KEY: misc_feature
<222> LOCATION: (67)..(68)
<223> OTHER INFORMATION: n stands for a, u, g or c.
<220> FEATURE:
<221> NAME/KEY: misc_feature
<222> LOCATION: (70)..(71)
<223> OTHER INFORMATION: n stands for a, u, g or c.

<400> SEQUENCE: 39
augnnunnun nunnunnunn unnunnunnu nnunnunnun nunnuaugnn unnunnuugc     60
nnunnunnun nugguagcgg cagcggcagc uag                                  93

<210> SEQ ID NO 40
<211> LENGTH: 51
<212> TYPE: RNA
<213> ORGANISM: Artificial Sequence
<220> FEATURE:
<223> OTHER INFORMATION: mRNA sequence

<400> SEQUENCE: 40
auggcccgcc accuugcuau gguuguugac uguaucgacc gcuccaucua a               51

<210> SEQ ID NO 41
<211> LENGTH: 51
<212> TYPE: RNA
<213> ORGANISM: Artificial Sequence
<220> FEATURE:
<223> OTHER INFORMATION: mRNA sequence

<400> SEQUENCE: 41
auggcccgcc accuugcuau gguuguugac aagaucgacc gcuccaucua a               51

<210> SEQ ID NO 42
<211> LENGTH: 16
<212> TYPE: PRT
<213> ORGANISM: Artificial Sequence
```

```
<220> FEATURE:
<223> OTHER INFORMATION: amino acid sequence
<220> FEATURE:
<221> NAME/KEY: MOD_RES
<222> LOCATION: (1)..(1)

<400> SEQUENCE: 42

Met Ala Arg His Leu Ala Met Val Gly Asp Lys Ile Asp Arg Ser Ile
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: amino acid sequence
<220> FEATURE:
<221> NAME/KEY: MOD_RES
<222> LOCATION: (1)..(1)
<223> OTHER INFORMATION: FORMYLATION

<400> SEQUENCE: 43

Met Ala Arg His Leu Ala Met Val Gly Asp Cys Ile Asp Arg Ser Ile
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: amino acid sequence not forming a croslinked
      structure
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (7)..(7)
<223> OTHER INFORMATION: Xaa stands for 2-amino-7-chlorohepto-5-ynoic
      acid.

<400> SEQUENCE: 44

Met Ala Arg His Leu Ala Xaa Val Gly Asp Lys Ile Asp Arg Ser Ile
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: amino acid sequence forming crosslinked
      structure
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (7)..(7)
<223> OTHER INFORMATION: Xaa stands for 2-amino-7-chlorohepto-5-ynoic
      acid.

<400> SEQUENCE: 45

Met Ala Arg His Leu Ala Xaa Val Gly Asp Cys Ile Asp Arg Ser Ile
1               5                   10                  15
```